(12) United States Patent
Choo et al.

(10) Patent No.: US 7,262,055 B2
(45) Date of Patent: Aug. 28, 2007

(54) REGULATED GENE EXPRESSION IN PLANTS

(75) Inventors: Yen Choo, Cambridge (GB); Christopher Graeme Ullman, London (GB); Nam-Hai Chua, Scarsdale, NY (US); Juan Pablo Sanchez, New York, NY (US)

(73) Assignees: Gendaq Limited, London (GB); The Rockefeller University, New York, NY (US)

( * ) Notice: Subject to any disclaimer, the term of this patent is extended or adjusted under 35 U.S.C. 154(b) by 415 days.

(21) Appl. No.: 09/732,348

(22) Filed: Dec. 7, 2000

(65) Prior Publication Data

US 2002/0046419 A1  Apr. 18, 2002

Related U.S. Application Data

(63) Continuation-in-part of application No. PCT/GB00/02071, filed on May 30, 2000, which is a continuation-in-part of application No. 09/139,762, filed on Aug. 25, 1998, now Pat. No. 6,013,453, which is a continuation of application No. 08/793,708, filed on Aug. 17, 1995.

(30) Foreign Application Priority Data

May 28, 1999 (GB) ................... 9912635.1
Jan. 24, 2000 (GB) ................... 0001578.4
Jan. 24, 2000 (GB) ................... 0001580.0

(51) Int. Cl.
*C12N 15/82* (2006.01)

(52) U.S. Cl. ..................... 435/419; 536/23.4

(58) Field of Classification Search ............. 435/320.1, 435/419, 468; 800/278, 298; 257/296, 368
See application file for complete search history.

(56) References Cited

U.S. PATENT DOCUMENTS

| 4,873,191 | A | 10/1989 | Wagner et al. |
|---|---|---|---|
| 5,175,384 | A | 12/1992 | Krimpenfort et al. |
| 5,175,385 | A | 12/1992 | Wagner et al. |
| 5,223,409 | A | 6/1993 | Ladner et al. |
| 5,260,203 | A | 11/1993 | Ladner et al. |
| 5,322,938 | A | 6/1994 | McPherson et al. |
| 5,352,605 | A | 10/1994 | Fraley et al. |
| 5,489,520 | A | 2/1996 | Adams et al. |
| 5,550,318 | A | 8/1996 | Adams et al. |
| 5,556,752 | A | 9/1996 | Lockhart et al. |
| 5,830,721 | A | 11/1998 | Stemmer et al. |
| 5,837,832 | A | 11/1998 | Chee et al. |
| 5,874,265 | A | 2/1999 | Adams et al. |
| 6,007,988 | A | 12/1999 | Choo et al. |
| 6,013,453 | A | 1/2000 | Choo et al. |
| 6,140,081 | A | 10/2000 | Barbas |
| 6,140,466 | A | 10/2000 | Barbas, III et al. |
| 6,242,568 | B1 | 6/2001 | Barbas, III et al. |
| 6,534,261 | B1 * | 3/2003 | Cox et al. ................ 435/6 |

FOREIGN PATENT DOCUMENTS

| EP | 0 249 432 | 2/1990 |
|---|---|---|
| EP | A-332104 | 3/1991 |
| EP | 0 317 511 | 10/1991 |
| EP | 412006 B1 | 6/1994 |
| EP | 0 359 472 | 12/1995 |
| EP | A-344029 | 1/1997 |
| EP | 0 385 962 | 7/2001 |
| EP | 412911 B1 | 7/2001 |
| WO | WO87/07299 | 12/1987 |
| WO | WO89/10396 | 11/1989 |
| WO | WO91/10741 | 7/1991 |
| WO | WO92/02536 A1 | 8/1991 |
| WO | WO92/04454 | 3/1992 |
| WO | WO93/07278 | 4/1993 |
| WO | WO94/13822 | 6/1994 |
| WO | WO95 19431 | 9/1994 |
| WO | WO95 11922 | 10/1994 |
| WO | WO95/33818 | 12/1995 |
| WO | WO96/06166 | 2/1996 |
| WO | WO96/32475 | 10/1996 |
| WO | WO97/49989 | 12/1997 |
| WO | WO98 54311 | 5/1998 |
| WO | WO98/49557 | 11/1998 |
| WO | WO98/53057 | 11/1998 |
| WO | WO98/53058 | 11/1998 |

(Continued)

OTHER PUBLICATIONS

Putterill J, Robson F, Lee K, Simon R, Coupland G. The CONSTANS gene of *Arabidopsis* promotes flowering and encodes a protein showing similarities to zinc finger transcription factors. Cell. Mar. 24, 1995;80(6):847-57.*

Aoyama T. et al. A glucocorticoid-mediated transcriptional induction system in transgenic plants. Plant J. Mar. 1997;11(3):605-12.*

Kim Y.G. et al. Hybrid restriction enzymes: zinc finger fusions to Fok I cleavage domain. Proc Natl Acad Sci U S A. Feb. 6, 1996;93(3):1156-60.*

Puchta H. et al. Two different but related mechanisms are used in plants for the repair of genomic double-strand breaks by homologous recombination. Proc Natl Acad Sci U S A. May 14, 1996;93(10):5055-60.*

Takatsuji H. et al: "Zinc-finger transcription factors in plants" Cell. Mol. Life Sci., vol. 54, pp. 582-596, 1998.

Klug, Aaron: "Zinc Finger peptides for the regulation of gene expression" J. Mol. Biol., vol. 293, pp. 215-218, 1999.

Dickinson, Liliane A. et al: "Inhibition of Ets-1 DNA binding and ternary complex formation between Ets-1, NF-kappaB, and DNA by a designed DNA-binding ligand" Journal of Biochemistry, vol. 274, No. 18, pp. 12765-12773, 1999.

(Continued)

*Primary Examiner*—Cynthia Collins
(74) *Attorney, Agent, or Firm*—Robins & Pasternak LLP

(57) ABSTRACT

A method is provided of regulating transcription in a plant cell from a DNA sequence comprising a target DNA operably linked to a coding sequence, which method comprises introducing an engineered zinc finger polypeptide in said plant cell which polypeptide binds to the target DNA and modulates transcription of the coding sequence.

20 Claims, 6 Drawing Sheets

FOREIGN PATENT DOCUMENTS

| | | |
|---|---|---|
| WO | WO98/53059 | 11/1998 |
| WO | WO98/53060 | 11/1998 |
| WO | WO99/02671 | 1/1999 |
| WO | WO99 47656 | 3/1999 |
| WO | WO99/45132 | 9/1999 |
| WO | WO 00 41566 A | 1/2000 |
| WO | WO 00 42219 A | 1/2000 |
| WO | WO 00/23464 | 4/2000 |
| WO | WO 01/52620 | 7/2001 |

OTHER PUBLICATIONS

Dickinson, Liliane A. et al: "Inhibition of RNA polymerase II transcription in human cells by synthetic DNA-binding ligands." Proceedings of the National Academy of Sciences of the United States, vol. 95, No. 22 pp. 12890-12895, 1998.
Nardelli, J. et al: "Zinc finger-DNA recognition: analysis of base specificity by site-directed mutagenesis", Nucleic Acids Research, vol. 20, No. 16, (IRL Press Ltd., Oxford, England), pp. 4137-4144, 1992.
Desjariais, J.R. and Berg, J.M.: "Toward rules relating zinc finger protein sequences and DNA binding site preference", Proc. Natl. Acad. Sci., vol. 89, No. 16, Natl. Acad. Sic., Washington, D.C., pp. 7345-7349, 1992.
Gottesfed et al: "Regulation of Gene Expression by Small Molecules" Nature, vol. 387, No. 6629 p. 202-205, 1997.
Gatz et al: "Stringent repression and homogenous de-repression by tetracycline of a modified CaMV 35S promoter in intact transgenic tobacco plants" Plant Journal, GB, Blackwell Scientific Publications, vol. 3, No. 2, pp. 397-404, 1992.
Weinmann et al: "A Chimeric Transactivator allows Tetracycline-responsive gene expression in whole plants" Plant Journal, GB, Blackwell Scientific Publications, vol. 5, No. 4, pp. 559-569, 1994.
Dudavera et al, (1996) Plant Cell 8: 1137-1148.
Bass et al, (1990)Proteins, 8: 309-314.
Bevan et al, (1989) Embo J. 8: 1899-1906.
Beerli et al, (1998) Proc. Natl. Acad. Sci. USA 95:14628-14633.
Bent et al (1994) Science 265: 1856-1860.
Berg, (1998) PNAS (USA) 85: 99-102.
Bevan et al (1983) Nature 304: 184-187.
McElroy et al, (1991) Mol. Gen. Genet. 231: 150-160.
Edwards and Coruzzi, (1989) Plant Cell 1: 241-248.
Elrod-Erickson et al, (1996) Structure 4: 1171-1180.
Wu et al (1995) PNAS USA 92: 344-348.
Van der Krol et al (1991) Plant Cell 3: 667-675.
Bevan. (1984) Nucl. Acids Res. 12: 8711-8721.
Fairall et al, (1993) Nature 366: 483-487.
Fiehn et al (2000) Nature Biotechnology 18:1157-1161.
MacMillin et al, (1997) Plant Physiol 113: 1369-1377.
Elrod-Erickson et al, (1988) Structure 6: 451-464.
Datta et al, (1990) Biotechnology 8: 736-740.
Devereux et al, (1984) Nucleic Acids Research 12:387.
Callis et al (1987) Genes Develop. 1: 1183-1200.
Choo and Klug, (1994) PNAS (USA) 91: 11163-67.
Choo et al, (1994) Nature 372: 642-645.
Choo, Y., et al, (1997) J. Mol.Biol 273: 525-532.
Potrykus (1991) Annu rev. Plant Physiol Plant Mol Biol, 42: 205-225.
Christou et al (1991) Biotechnology 9: 957-962.
Phillips et al, (1995) Plant Physiol 108: 1049-1057.
Estruch et al, (1994) Nucleic Acids Res. 22: 3983-89.
Hofgen & Willmitzer, (1988) Nucl. Acids Res. 16: 9877.
Williams et al, (1998) Plant Physiol 117: 559-563.
Logemann et al (1989) Plant Cell 1: 151-158.
Han et al (1993) EMBO J. 12: 2723-2733.
Afshar et al, (1999): Curr. Op. Biotech. vol. 10, 59-63.
Goff et al, (1991) Genes Dev. 5: 298-309.
Goodrich et al. (1996), Cell 84:825-830.
Gouldson, P.R. et al, (2000) Neuropsychopharmacology 23: S60-S77.
Jamieson et al (1994) Biochem. 33: 5689-5695.
Grimes et al, (1996) Mol Cell. Biol. 16: 6263-6272.
Ho, et al, Nature (1996) 382: 822-826.
Suzuki et al, (1994) NAR 22: 3397-3405.
Tao, H. & Umek, R.M. (1999) DNA Cell Biol 18: 75-84.
Fromm et al (1990) Biotechnology 8: 833-839.
Jefferson et al, (1987) Embo J. 6: 3901-3907.
Koziel et al (1993) Biotechnology 11: 194-200.
Genbank Accession No. X07937.1.
Goff et al, (1992) Genes Dev. 6: 864-75.
Lee et al, Science (1989) 245:635-637.
Krizek et al, (1991) J. Am. Chem. Soc. 113: 4518-4523.
Fairall et al, (1993) Nature (London) 366, 483-487.
Kim et al, (1996) Proc. Natl. Acad. Sci. USA 93:1156-1160.
Klein et al (1987) Nature 327: 70-73.
Mariani et al (1990) Nature 347: 737-741.
Mariani et al (1992) Nature 357: 384-387.
Markland et al (1987) Mol. Cell Biol. 7: 4255-4265.
Pavletich & Pabo (1991) Science 252, 809-817.
Liu et al, (1997) Proc. Natl. Acad. Sci. USA 94:5525-5530.
Pomerantz et al, (1998) Science 267:93-96.
Pavletich and Pabo, (1993) Science 261: 1701-1707.
Prasher et al (1992) Gene 111: 229-233.
Suzuki et al, (1994):PNAS, 91: 12357-61.
Ross et al, (1999) Arch. Biochem. Biophys. 367:9-16.
Ralston et al, (1988) Genetics 119: 185-197.
Rothstein et al (1987) Gene 53: 153-161.
Sadowski, (1993), FASEB J. 7:760-767.
Turpen et al. (1993) J. Virol. Methods, 42: 227-239.
White et al (1990) Nucl. Acids Res. 18: 1062.
Vasil et al (1992) Biotechnology 10: 667-674.
Thomas et al, (1999) PNAS 96: 4698-4703.
Sainz et al, (1997), Mol. Cell. Biol. 17: 115-22.
Mattheakis et al, (1994) Proc Natl Acad Sci U.S.A., 91: 9022-6.
Mc Elroy et al (1991) Mol. Gen Genet. 231: 150-160.
Pomeranz, et al, (1982) Biochem. 37:965.
Messing & Vierra (1982) Gene 19: 259-268.
Schmitz, M. et al (1995) J. Biol. Chem. 270: 15576-15584.
Miller et al, (1985) EMBO J. 4:1609-1614.
Vasil et al (1993) Biotechnology 11: 1553-1338.
Murray et al (1989) Nucl. Acids Res. 17: 477-498.
Nagaoka, M., et al, (1994) J. Am. Chem. Soc. 116:4085-4086.
Finnegan et al (1994) Bio/Technol. 12: 883-888.
Moosmann et al, (1997) Biol. Chem. 378: 669-677.
Nolte, R.T. et al, (1998) Proc. Natl. Acad. Sci. USA 95:2938-2943.
O'Shea, Science (1991), 254:539-544.
Guyer et al (1998) Genetics 149: 633-639.
Rebar & Pabo (1994) Science 263:671-673.
Reich et al (1986) Biotechnology 4: 1001-1004.
Schwechheimer et al (1998) Plant Mol Biol 36(2): 195-204.
Tok and Rando (1998): J. Am. Soc. Chem. vol. 120 8279-8280.
Tsai and Coruzzi, (1990) EMBO J 9: 323-332.
Choo Y, Klug A: Designing DNA-binding proteins on the surface of filamentous phage. Curr. Opin. Biotech. 1995, 6:431-436.
Choo Y, Klug A: Toward a code for the interactions of zinc fingers with DNA: Selection of randomised zinc fingers displayed on phage. Proc. Natl. Acad. Sci. U.S.A. 1994, 91:11163-11167.
Isalan M, Choo Y, Klug A: Synergy between adjacent zinc fingers in sequence-specific DNA recognition Proc Natl Acad Sci 1997, 94:5617-5621.
Isalan M, Klug A, Choo Y: Comprehensive DNA recognition through concerted interactions from adjacent zinc fingers. Biochemistry 1998, 37:12026-12033.
Greisman HA, Pabo CO: A general strategy for selecting high-affinity zinc finger proteins for diverse DNA target sites. Science 1997, 275:657-661.
Segal DJ, Dreier B, Beerli RR, Barbas CF: Toward controlling gene expression at will selection and design of zinc finger domains recognising each of the 5'-GNN-3' DNA target sequences. Proc. Natl. Acad. Sci. USA 1999, 96:2758-2763.
Isalan MD, Klug A, Choo Y: A rapid universal method to engineer zinc fingers illustrated by targeting the HIV-1 promoter. Submitted 2000.

Kim J-S, Pabo CO: Getting a handhold on DNA: design of poly-zinc finger proteins with fermtomolar dissociation constants. Proc. Natl. Acad. Sci. USA 1998, 95:2812-2817.

Kim J-S, Kim J, Cepek KL, Sharp PA, Pabo CO: Design of TATA box-binding protein/zinc finger fusions for targeted regulation of gene expression. Proc Natl Acad Sci USA 1997, 94:3616-3620.

Kim J-S, Pabo CO: Transcriptional repression by zinc finger peptides. The Journal of Biological Chemistry 1997, 272:29795-29800.

Choo Y, Castellanos A, Garcia-Hernandez B, Sanchez-Garcia I, Klug A: Promoter-specific activation of gene expression directed by bacteriophage-selected zinc fingers. J. Mol. Biol. 1997, 273:525-532.

Beerli RR, Segal DJ, Dreier B, Barbas CF: Toward controlling gene expression at will specific regulation of the erbB-2/HER-2 promoter by using polydactyl zinc finger proteins constructed from modular building blocks. Proc Natl Acad Sci USA 1998, 95:14628-14633.

Beerli RR, Dreier B, Barbas CF: Positive and negative regulation of endogenous genes by designed transcription factors. Proc Natl Acad Sci 2000, 97:1495-500.

Chandrasegaran S, Smith J: Chimaeric restriction enzymes: what is next? J Biol Chem 1999, 380:841-8.

Bushman FD, Miller MD: Tethering human immunodeficiency virus type 1 preintegration complexes to target DNA promotes integration at nearby sites. J Virol 1997, 71:458-64.

Xu G-L, Bestor TH: Cytosine methylation targeted to predetermined sequences. Nat Genet 1997, 17:376-378.

Choo Y: Recognition of DNA methylation by zinc fingers. Nature Struct. Biol. 1998, 5:264-265.

Desjarlais JR, Berg JM: Use of a zinc finger consensus sequence framework and specificity rules to design specific DNA binding proteins. Proc. Natl. Acad. Sci. USA 1993, 90:2256-2260.

Choo Y, Klug A: Selection of DNA binding sites for zinc fingers using rationally randomised DNA reveals coded interactions. Proc. Natl. Acad. Sci. U.S.A. 1994, 91:11168-11172.

Corbi N, Perez M, Maione R, Passananti C: Synthesis of a new zinc finger peptide; comparison of its 'code' deduced and 'CASTing' derived binding sites. FEBS Letters 1997, 417:71-74.

Corbi N, Libri V, Fanciulli M, Passananti C: Binding properties of the artificial zinc fingers coding gene Sint1. Biochemical and Biophysical Research Communications 1998, 253:686-692.

Isalan M, Choo Y: Engineered zinc finger proteins that recognise DNA modification by HaeIII and HhaI Methyltransferase enzymes. J Mol Biol 2000, 295:471-477.

Wolfe SA, Greisman HA, Raman EL, Pabo CO: Analysis of zinc fingers optimised via phage display: evaluating the utility of a recognition code. J. Mol. Biol. 1999, 285:1917-1934.

Pomerantz JL, Wolfe SA, Pabo CO: Structure-based design of a dimeric zinc finger protein. Biochemistry 1998, 37:965-970.

Wang BS, Pabo CO: Dimerisation of zinc fingers mediated by peptides evolved in vitro from random sequences. Proc. Natl. Acad. Sci. USA 1999, 96:9568-9573.

Nakaseko Y, Neuhaus D, Klug A, Rhodes D: Adjacent zinc-finger motifs in multiple zinc-finger peptides from SW15 form structurally independent, flexibly linked domains. J. Mol. Biol. 1992, 228:619-36.

Kamiuchi T, Abe E, Imanishi M, Kaji T, Nagaoka M, Sugiura Y: Artificial nine zinc-finger peptide with 30 base pair binidng sites. Biochemistry 1998, 37:13827-34.

Nahon E, Raveh D: Targeting a truncated HO-endonuclease of yeast to novel DNA sites with foreign zinc fingers. Nucleic Acids Res 1998, 26:1233-1239.

Smith J, Berg JM, Chandrasegaran S: A detailed study of the substrate specificity of a chimaeric restriction enzyme. Nucleic acids Res 1999, 27:674-81.

Carroll D, Segal DJ, Trautman JK, Smith J, Kim Y-G, Chandrasegaran S: Stimulation of homologous recombination through targeted cleavage by a chimeric nuclease. Proc Natl Acad Sci USA 1999 In press.

Foster R, and Chua, N. H. (1999). An *Arabidopsis* mutant with deregulated ABA gene expression: implications for negative regulator function. Plant J 17, 363-372.

Zuo, J., Niu Q. W., and Chua, N. H. (2000). An estrogen receptor-based trransactivator XVE mediates highly inducible gene expression in transgenic plants. Plant Journal 24, 265-273.

Taylor, J. et al., (1995) Biological and immunogenic properties of a canarypox-rabies recombinant, ALVAC-RG (vCP65) in non-avain species. Vaccine 23(6), 519-610.

Bibkova, M. et al. "Stimulation of Homologous Recombination through Targeted Cleavage by Chimeric Nuclease" Molecular and Cellular Biology, 2001 21(1):289-297.

Choo, Y. and Klug A. "Physical basis of a protein-DNA recognition code" Current Opinion in Structural Biology, 1997 7(1):117-125.

Hajdukiewicz, P. et al. "The small, versatile pPZP family of *Agrobacterium* binary vectors for plant transformation" Plant Molecular Biology, 1994 25(6):989-994.

Isalan, M. et al. "A rapid, generally applicable method to engineer zinc fingers illustrated by targeting the HIV-1 promoter" Nature Biotechnology, 2001 19(7):656-660.

Schwechheimer C, Smith C, Bevan MW, "The activities of acidic and glutamine-rich transcriptional activation domains in plant cells: design of modular transcription factors for high-level expression." Plant Mol Biol, vol. 36(2):195-204, 1998.

Aoyama T, Chua NH. "A glucocorticoid-mediated transcriptional inductin system in transgenic plants." Plant J MAR; vol. 11(3):605-612, 1997.

J. Zuo, Q.-W. Niu and N.-H. Chua "An estrogen receptor-based transactivator XVE mediated highly inducible gene expression in transgenic plants" Plant J. vol. 24, Issue 2, Oct. 2000.

N. Dudareva, J.C. D'Auria, K.H. Nam, R.A. Raguso and E. Pichersky "Acetyl-CoA:benzylalcohol acetyltransferase—an enzyme involved in floral scent production in *Clarkia breweri*" Plant J. vol. 14, Issue 3, 297-304, May 1998.

Liz J. Richter, Yasmin Thanavala, Charles H. Arntzen, Hug S. Mason, "Production of hepatitis B surface antigen in transgenic plants for oral immunization", Nature Biotechnology vol. 18, 1167-1171 (Nov. 1, 2000).

Tim Kunkel, Qi-Wen Niu, Yang-Sun Chan, Nam-Hai Chua, "Inducible isopenenyl transferase as a high-efficiency marker for plant transformation", Nature Biotechnology vol. 17, 916-919 (Sep. 1, 1999).

Martha L. Bulyk, Erik Gentalen, David J. Lockhart, George M. Church, "Quantifying DNA-protein interactions by double stranded: DNA arrays", Nature Biotechnology vol. 17, 573-577 (Jun. 1, 1999).

* cited by examiner

Zinc finger chimera

Reporter construct

First series pBA002

Second series pER8

Reporter construct of second series

- estrogen

+Estrogen (17Bestradiol)   -Estrogen

0 Hr β-17-ESTRADIOL

20 Hr β-17-ESTRADIOL pBA4XBSLUC pBA4XBSLUC AND
pER8TFIIIAZIFVP16

SEQUENCE LISTING

```
<160> NUMBER OF SEQ ID NOS:   21

<210> SEQ ID NO 1
<211> LENGTH: 17
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Plant translational initiation context sequence

<400> SEQUENCE: 1
aaggagatat aacaatg                                                    17

<210> SEQ ID NO 2
<211> LENGTH: 10
<212> TYPE: DNA
<213> ORGANISM: Artificial Sequence
```

```
<220> FEATURE:
<221> NAME/KEY: misc_feature
<222> LOCATION: (1)..(7)
<223> OTHER INFORMATION: plant translational initiation context sequence

<400> SEQUENCE: 2
gtcgaccatg                                                          10

<210> SEQ ID NO 3
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: oligonucleotide

<400> SEQUENCE: 3
ctcctgcagt tggacctgtg ccatggccgg ctgggccgca tagaatggaa caactaaagc   60

<210> SEQ ID NO 4
<211> LENGTH: 995
<212> TYPE: DNA
<213> ORGANISM: Artificial Sequence
<220> FEATURE:
<221> NAME/KEY: misc_feature
<222> LOCATION: (15)..(17)
<223> OTHER INFORMATION: translational initiating ATG
<221> NAME/KEY: misc_feature
<222> LOCATION: (16)..(416)
<223> OTHER INFORMATION: Fingers 1 to 4 of TFIIIA
<221> NAME/KEY: misc_feature
<222> LOCATION: (308)..(416)
<223> OTHER INFORMATION: spacer
<221> NAME/KEY: misc_feature
<222> LOCATION: (417)..(689)
<223> OTHER INFORMATION: three fingers of zinc fingers protein Zif268
<221> NAME/KEY: misc_feature
<222> LOCATION: (701)..(722)
<223> OTHER INFORMATION: Nuclear Localization Signal
<221> NAME/KEY: misc_feature
<222> LOCATION: (957)..(986)
<223> OTHER INFORMATION: c-myc tag

<400> SEQUENCE: 4
tctagagcgc cgccatggga gagaaggcgc tgccggtggt gtataagcgg tacatctgct   60 cttcgccga ctgcggcgct gcttataaca agaactggaa actgcaggcg catctgtgca  120
aacacacagg agagaaacca tttccatgta aggaagaagg atgtgagaaa ggctttacct  180
cgcttcatca cttaacccgc cactcactca ctcatactgg cgagaaaaac ttcacatgtg  240
actcggatgg atgtgacttg agatttacta caaaggcaaa catgaagaag cactttaaca  300
gattccataa catcaagatc tgcgtctatg tgtgccattt tgagaactgt ggcaaagcat  360
tcaagaaaca caatcaatta aaggttcatc agttcagtca cacacagcag ctgccgtatg  420
cttgccctgt cgagtcctgc gatcgccgct tttctcgctc ggatgagctt acccgccata  480
tccgcatcca cacaggccag aagcccttcc agtgtcgaat ctgcatgcgt aacttcagtc  540
gtagtgacca ccttaccacc cacatccgca cccacacagg cgagaagcct tttgcctgtg  600
acatttgtgg gaggaagttt gccaggagtg atgaacgcaa gaggcatacc aaaatccatt  660
taagacagaa ggacgcggcc gcactcgagc ggaattccgg cccaaaaaag aagagaaagg  720
tcgccccccc gaccgatgtc agcctggggg acgagctcca cttagacggc gaggacgtgg  780
cgatggcgca tgccgacgcg ctagacgatt cgatctggga catgttgggg gacgggatt   840 ccccggggcc gggatttacc ccccacgact ccgcccccta cggcgctctg gatacggccg  900
```

```
acttcgagtt tgagcagatg tttaccgatg cccttggaat tgacgagtac ggtggggaac    960
aaaaacttat ttctgaagaa gatctgtaag gatcc                              995

<210> SEQ ID NO 5
<211> LENGTH: 947
<212> TYPE: DNA
<213> ORGANISM: Artificial Sequence
<220> FEATURE:
<221> NAME/KEY: misc_feature
<222> LOCATION: (723)..(908)
<223> OTHER INFORMATION: transactivation domain of VP64, other features
      except c-myc tag (listed below) same as SEQ ID NO:
<221> NAME/KEY: misc_feature
<222> LOCATION: (909)..(938)
<223> OTHER INFORMATION: c-myc tag, other features except
      transactivation domain VP64 (listed above) same as SEQ ID NO:

<400> SEQUENCE: 5
tctagagcgc cgccatggga gagaaggcgc tgccggtggt gtataagcgg tacatctgct    60 cttttcgccga ctgcggcgct gcttataaca agaactggaa actgcaggcg catctgtgca   120
aacacacagg agagaaacca tttccatgta aggaagaagg atgtgagaaa ggctttacct   180
cgcttcatca cttaacccgc cactcactca ctcatactgg cgagaaaaac ttcacatgtg   240
actcggatgg atgtgacttg agatttacta caaaggcaaa catgaagaag cactttaaca   300
gattccataa catcaagatc tgcgtctatg tgtgccattt tgagaactgt ggcaaagcat   360
tcaagaaaca caatcaatta aaggttcatc agttcagtca cacacagcag ctgccgtatg   420
cttgccctgt cgagtcctgc gatcgccgct tttctcgctc ggatgagctt acccgccata   480
tccgcatcca cacaggccag aagcccttcc agtgtcgaat ctgcatgcgt aacttcagtc   540
gtagtgacca ccttaccacc cacatccgca cccacacagg cgagaagcct tttgcctgtg   600
acatttgtgg gaggaagttt gccaggagtg atgaacgcaa gaggcatacc aaaatccatt   660
taagacagaa ggacgcggcc gcactcgagc ggaattccgg cccaaaaaag aagagaaagg   720
tcgaacttca gctgacttcg gatgcattag atgactttga cttagatatg ctaggatctg   780
acgcgctaga cgatttcgat ctggacatgt tgggcagcga tgctctagac gatttcgatt   840
tagatatgct tggctcggat gccctggatg acttcgacct cgacatgctg tcaagtcagc   900
tgagccagga acaaaaactt atttctgaag aagatctgta aggatcc                  947

<210> SEQ ID NO 6
<211> LENGTH: 14
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: plant translational initiation context sequence

<400> SEQUENCE: 6
aaggagatat aaca                                                      14

<210> SEQ ID NO 7
<211> LENGTH: 29
<212> TYPE: DNA
<213> ORGANISM: Artificial Sequence
<220> FEATURE:
<221> NAME/KEY: protein_bind
<222> LOCATION: (1)..(29)
<223> OTHER INFORMATION: target DNA sequence

<400> SEQUENCE: 7
```

```
tgcgtgggcg tgtacctgga tgggagacc                                           29
```

```
<210> SEQ ID NO 8
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: forward primer

<400> SEQUENCE: 8
ccacgcgtcc atgggagaga aggcgctgcc ggtgg                                    35
```

```
<210> SEQ ID NO 9
<211> LENGTH: 44
<212> TYPE: DNA
<213> ORGANISM: Artificial Sequence
<220> FEATURE:
<221> NAME/KEY: misc_feature
<222> LOCATION: (1)..(44)
<223> OTHER INFORMATION: reverse primer

<400> SEQUENCE: 9
ccactagtcc ttacagatct tcttcagaaa taagttttg ttcc                           44
```

```
<210> SEQ ID NO 10
<211> LENGTH: 148
<212> TYPE: DNA
<213> ORGANISM: Artificial Sequence
<220> FEATURE:
<221> NAME/KEY: misc_feature
<222> LOCATION: (1)..(148)
<223> OTHER INFORMATION: Sense strand primer

<400> SEQUENCE: 10
cctctagatc ggtctcccat ccaggtacac gcccacgcaa gtcggtctcc catccaggta        60
cacgcccacg caagtcggtc tcccatccag gtacacgccc acgcaagtcg gtctcccatc        120
caggtacacg cccacgcaag aagcttcc                                            148
```

```
<210> SEQ ID NO 11
<211> LENGTH: 148
<212> TYPE: DNA
<213> ORGANISM: Artificial Sequence
<220> FEATURE:
<221> NAME/KEY: misc_feature
<222> LOCATION: (1)..(148)
<223> OTHER INFORMATION: antisense strand primer

<400> SEQUENCE: 11
ggaagcttct tgcgtgggcg tgtacctgga tgggagaccg acttgcgtgg gcgtgtacct        60
ggatgggaga ccgacttgcg tgggcgtgta cctggatggg agaccgactt gcgtgggcgt        120
gtacctggat gggagaccga tctagagg                                            148
```

```
<210> SEQ ID NO 12
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: forward primer

<400> SEQUENCE: 12
```
ccagatctgg tctcccatcc aggtacacgc ccacgcaaga tctcc            45

<210> SEQ ID NO 13
<211> LENGTH: 46
<212> TYPE: DNA
<213> ORGANISM: Artificial Sequence
<220> FEATURE:
<221> NAME/KEY: misc_feature
<222> LOCATION: (1)..(46)
<223> OTHER INFORMATION: reverse primer

<400> SEQUENCE: 13
ggagatcttg cgtgggcgtg tacctggatg ggagaccaga tctcgg           46

<210> SEQ ID NO 14
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: forward primer

<400> SEQUENCE: 14
ccccatggtg agcaagggcg aggagctgtt cacc                        34

<210> SEQ ID NO 15
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: reverse primer

<400> SEQUENCE: 15
ccgaattctt acttgtacag ctcgtccatg ccgag                       35

<210> SEQ ID NO 16
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: forward primer

<400> SEQUENCE: 16
ccctcgagcg gggtaccgcg ggcccggg                               28

<210> SEQ ID NO 17
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: reverse primer

<400> SEQUENCE: 17
cagttggaat tctagagtcg cggccgctac                             30

<210> SEQ ID NO 18
<211> LENGTH: 38
<212> TYPE: DNA
<213> ORGANISM: Artificial Sequence
<220> FEATURE:
<221> NAME/KEY: misc_feature

```
<222> LOCATION: (1)..(38)
<223> OTHER INFORMATION: forward primer

<400> SEQUENCE: 18
ccgctcgagg ccccccgac cgatgtcagc ctggggga                              38

<210> SEQ ID NO 19
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: reverse primer

<400> SEQUENCE: 19
ccgctcgagt attaatttga gaatgaacaa aaaggacc                             38

<210> SEQ ID NO 20
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: forward primer

<400> SEQUENCE: 20
gccattaatc ggaatgggag agaaggcgct gccggtgg                             38

<210> SEQ ID NO 21
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: reverse primer

<400> SEQUENCE: 21
gcctattaat ttgagaatga acaaaaagga cc                                   32
```

REGULATED GENE EXPRESSION IN PLANTS

REFERENCE TO RELATED APPLICATIONS/INCORPORATION BY REFERENCE

This application is a continuation-in-part of PCT application no. PCT/GB00/02071 entitled "GENE SWITCHES" filed 30 May 2000 and published on Dec. 7, 2000 as WO 00/73434, designating the US and claiming priority from GB applications 9912635.1 filed 28 May 1999 and Great Britain applications 0001580.0 and 0001578.4, both of which were filed 24 Jan. 2000. Further mentioned and incorporated by reference herein are PCT/GB99/03730, filed Nov. 9, 1999, published as WO00/27878A1 on May 18, 2000 entitled "Screening System For Zinc Finger Polypeptides For A Desired Binding Ability" and claiming priority from GB application 9824544.2, filed Nov. 9, 1998, and designating the US; PCT/GB99/03730 which is a continuation-in-part of U.S. patent application Ser. No. 09/139,762, filed Aug. 25, 1998 (now U.S. Pat. No. 6,013,453), which is a continuation of U.S. patent application Ser. No. 08/793,408 (now U.S. Pat. No. 6,007,988), filed as PCT application no. PCT/GB95/01949 on Aug. 17, 1995, designating the U.S. and, published as WO96/06166 on Feb. 29, 1996 entitled "Improvements in or Relating to Binding Proteins for Recognition of DNA"; PCT/GB95/01949 claims the benefit of priority from GB application 9514698.1, filed Jul. 18, 1995, GB application 9422534.9, filed Nov. 8, 1994 and GB application no. 9416880.4, filed Aug. 20, 1994. Mention is also made of: U.S. Ser. No. 08/422,107; WO96/32475; WO99/47656A2, published Sep. 23, 1999 entitled "Nucleic Acid Binding Proteins"; WO98/53060A1, published Nov. 26, 1998 entitled "Nucleic Acid Binding Proteins"; WO98/53059A1 published Nov. 26, 1998 entitled "Nucleic Acid Binding Proteins"; WO98/53058A1 published Nov. 26, 1998 entitled "Nucleic Acid Binding Proteins"; WO98/53057A1 published Nov. 26, 1998 entitled "Nucleic Acid Binding Polypeptide Library"; U.S. Pat. Nos. 6,013,453 and 6,007,988; Fiehn et al. (2000) Nature Biotechnol. 18:1157-1161; Richter et al. (2000) Nature Biotechnol. 18:1167-1171; and, generally, Nature Biotechnol. Vol. 18(11) together with all documents cited or referenced therein. Each of the foregoing applications and patents, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

STATEMENT OF RIGHTS TO INVENTIONS MADE UNDER FEDERALLY SPONSORED RESEARCH

Not applicable.

TECHNICAL FIELD

This invention relates to the regulation of gene expression in plants using engineered zinc fingers that bind to sequences within gene regulatory sequences. Moreover, this invention also relates to transgenic plants that comprise engineered zinc finger-containing peptides.

BACKGROUND OF THE INVENTION

The application of biotechnology to plants has yielded many agricultural gains. For example, biotechnology has been used to improve various properties of plants such as resistance to pests and diseases, resistance to herbicides, and the improvement of various seed and fruit traits. Many further applications of plant biotechnology are anticipated and these include the modification of specific traits that may be of agronomic interest or of interest in the processing and use of plant-derived products. In many instances, this could be undertaken by the manipulation of endogenous genes which encode these traits, however, the sophisticated means to achieve up- and down-regulation of such endogenous genes is, in many cases, not yet available. In addition, plants also hold great promise as biological "factories" for a variety of chemical products including enzymes and compounds for industrial and pharmaceutical use. However, it is expected that the continuous production of high concentrations of gene products and compounds for such use may have deleterious consequences for the host plant and consequently, more sophisticated mechanisms for expressing such genes are required.

Accordingly, gene switches are currently of interest for the control of timing and/or dosage of gene expression in plants. In particular, the development of gene switches that can be directed towards any gene in a plant chromosome is highly desirable.

SUMMARY OF THE INVENTION

The present invention seeks to overcome these difficulties by providing non-naturally occurring engineered zinc finger proteins to confer specificity on gene regulation for both endogenous genes and transgenes of interest. More specifically, the present invention can be used to regulate any gene in a plant.

Accordingly the present invention provides a method of regulating transcription in a plant cell which method comprises introducing an engineered zinc finger polypeptide into said plant cell which polypeptide binds to a target DNA and modulates transcription of a coding sequence which is operably linked to said target DNA.

Previously, it has been reported that engineered zinc fingers can be used to regulate genes in mammalian cells (see for example Choo et al., Nature 372: 642-645 (1994); Pomerantz et al, Science 267: 93-96 (1995); Liu et al. PNAS 94: 5525-5530 (1997); Beerli et al. PNAS 95: 14628-14633 (1998)). However, only in the case of Choo et al. was the regulated gene a gene integrated in a chromosome of the host mammalian cell. It is well recognized that the biology of mammalian and plant cells is very different and that each has evolved be very different at the structural, physiological, biochemical and molecular biological level. In the present invention, the inventors have shown for the first time that it is possible to regulate a gene in a plant using an engineered zinc finger. More specifically, the inventors have shown that, using an engineered zinc finger, a gene integrated in a plant chromosome can be regulated in a via binding of the engineered zinc finger to a target DNA sequence adjacent to the target gene.

The zinc fingers of the present invention can be used to up-regulate or down-regulate any gene in a plant. By designing a zinc finger with a transactivating domain the induction of an endogenous gene can be accomplished specifically and bypass any endogenous regulation of the targeted gene. Previously, the only available method was to introduce a transgene in another location of the genome under the regulation of a separate promoter. The zinc fingers of the present invention can also be used to down-regulate any gene in any plant, which has previously only been possible using techniques such as antisense, ribozymes and co-suppression, all of which are somewhat unpredictable. The zinc finger approach to down-regulation is highly potent and allows the targeting of specific member of a gene family without affecting the other members.

The term "engineered" means that the zinc finger has been generated or modified in vitro. It has therefore typically been produced by deliberate mutagenesis, for example the substitution of one or more amino acids, either as part of a random mutagenesis procedure or site-directed mutagenesis, or by selection from a library or libraries of mutated zinc fingers. Engineered zinc fingers for use in the invention can also be produced de novo using rational design strategies.

The term "introduced into" means that a procedure is performed on a plant, a plant part, or a plant cell such that the zinc finger polypeptide is then present in the cell or cells. Examples of suitable procedures include the microinjection, bombardment, agrobacterium transformation, electroporation, transfection or other transformation or delivery techniques of cells with a nucleic acid construct that is capable of directing expression of the zinc finger polypeptide in the cell, or the zinc finger protein itself.

The term "target DNA sequence" means any nucleic acid sequence to which a zinc finger is capable of binding. It is usually but not necessarily a DNA sequence within a plant chromosome, to which an engineered zinc finger is capable of binding. A target DNA sequence will generally be associated with a target gene (see below) and the binding of the engineered zinc finger to the gene will generally allow the up- or down-regulation of the associated gene. In one embodiment, the target DNA sequence is part of an endogenous genomic sequence. In another embodiment, the target DNA sequence and coding sequence have been introduced into the cell or are heterologous to the cell. In many cases, a target DNA sequence will form part of a promoter or other transcription regulatory region such as an enhancer. In a most preferred embodiment, the target DNA is a known sequence of a promoter from a plant gene of interest.

The term "target gene" means a gene in a plant or plant cell the expression of which one may wish to affect using the methods described in the present invention. A target gene may be an endogenous gene (i.e. one which is normally found in genome of the plant or plant cell) or a heterologous gene (i.e. one that does not normally exist in the genome of the plant or cell).

The term "heterologous to the cell" means that the sequence does not naturally exist in the genome of the cell but has been introduced into the cell. A heterologous sequence can include a modified sequence introduced at any chromosomal site, or which is not integrated into a chromosome, or which is introduced by homologous recombination such that it is present in the genome in the same position as the native allele.

In a highly preferred embodiment, the zinc finger polypeptide is fused to a biological effector domain. The term "biological effector domain" means any polypeptide that has a biological function and includes enzymes and transcriptional regulatory domains or proteins, and additional sequence such as nuclear localization sequences.

Preferably the zinc finger polypeptide is fused to a transcriptional activator domain or a transcriptional repressor domain.

In a further embodiment of the method of the invention the plant cell is part of a plant or can be regenerated into a plant and the target sequence is part of a regulatory sequence to which the nucleotide sequence of interest is operably linked.

The present invention further provides a plant cell comprising a polynucleotide encoding an engineered zinc finger polypeptide and a target sequence to which the zinc finger polypeptide binds.

The present invention also provides a transgenic plant comprising a polynucleotide encoding an engineered zinc finger polypeptide and a target sequence to which the zinc finger polypeptide binds.

The present invention further provides a transgenic plant comprising a polynucleotide encoding an engineered zinc finger polypeptide and a target sequence which is within a plant chromosome.

The present invention further provides a transgenic plant comprising a polynucleotide encoding an engineered zinc finger polypeptide and a target sequence which is within the sequence of a gene which is endogenous to the plant.

BRIEF DESCRIPTION OF THE DRAWINGS

In FIG. 5, a. is TFIIIAZIFVP16+4XBS-Luciferase, b. is TFIIIAZIFVP16+1XBS-Luciferase, c. is TFIIIAZIFVP64+4XBS-Luciferase, d. is TFIIIAZIFVP16+4XBS-Luciferase, e. is TFIIIAZIFVP64+4XBS-Luciferase, f. is 4XBS-Luciferase, g. is 1XBS-Luciferase, and h. is KIN2-Luciferase.

In FIG. 6, a. is pER8-TFIIIAZIFVP64+pIXBSluciferase (with estrogen), b. is pIXBSluciferase (with estrogen), c. is pER8-TFIIIAZIFVP64+pIXBSluciferase (without estrogen) and d. is pIXBSluciferase (without estrogen).

FIG. 7 FIG. 6 shows 17-β-Estradiol regulated expression of GFP. In FIG. 7, a. is pER8-TFIIIAZIFVP64+p4XBSGFP and b. is pER8-TFIIIAZIFVP16+p4XBSGFP

DETAILED DESCRIPTION OF THE INVENTION

Figure 1:
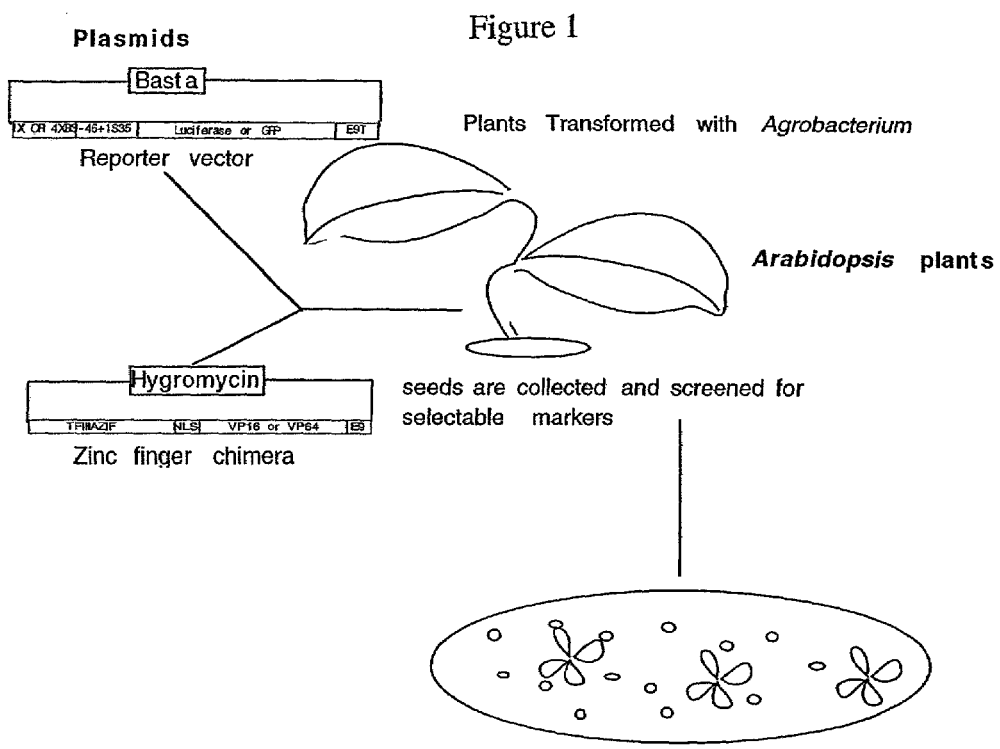
FIG. 1 is a general depiction of plasmids described herein and their use in transforming plants with *Agrobacterium*.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al. Molecular Cloning:A Laboratory Manual, 2d ed. (1989) Cold Spring Harbor Laboratory Press, Cold Spring Harbor, N.Y. and Ausubel et al. Short Protocols in Molecular Biology (1999) 4$^{th}$ Ed, John Wiley & Sons, Inc.), chemical methods, pharmaceutical formulations and delivery and treatment of patients.

A. Zinc Fingers

A zinc finger chimera is a transcription factor that comprises a DNA binding domain (comprising a number of zinc fingers), designed to bind specifically to any DNA sequence and one or more further domains. Usually, a nuclear localization domain is attached to the zinc finger domain to direct the chimera to the nucleus. Generally, the chimera also includes an effector domain that can be a transactivation or repression domain to regulate the expression of the gene in question. Choo and Klug (1995) Curr. Opin. Biotech. 6:431-436; Choo and Klug (1997); Rebar and Pabo (1994) Science 263:671-673; and Jamieson et al. (1994) Biochem. 33:5689-5695. The zinc finger chimera may also preferably include other domains which may be advantageous within the context of the present invention. For example, DNA modifying domains (such as endonucleases and methylases) can be added to the zinc finger domain, conferring to the zinc finger chimera the ability to regulate expression of the gene of interest or modify any DNA specifically. Wu et al. (1995) Proc. Natl. Acad. Sci. USA 92:344-348; Nahon and Raveh (1998); Smith et al. (1999; and Carroll et al. (1999). Zinc finger proteins of the Cys2-His2 class are preferred within the context of the present invention.

Zinc fingers are small protein domains that are able to recognize and bind a nucleic acid triplet, or an overlapping quadruplet, in a nucleic acid binding sequence. Preferably, there are 2 or more zinc fingers, for example 2, 3, 4, 5 or 6 zinc fingers, in each binding protein. Advantageously, there are 3 or more zinc fingers in each zinc finger binding protein.

All of the DNA binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide. Residues referred to as "++" are residues present in an adjacent (C-terminal) finger. Where there is no C-terminal adjacent finger, "++" interactions do not operate.

Zinc finger polypeptides according to the present invention are engineered. That is, essentially "man-made". Typically, zinc fingers according to the invention are produced by mutagenesis techniques or designed using rational design techniques. Zinc fingers can also be selected from randomized libraries using screening procedures, such as those described below.

replaced by a functional analogue thereof, particularly an artificial functional analogue. The nomenclature used herein therefore specifically comprises within its scope functional analogues or mimetics of the defined amino acids.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the—strand of the nucleic acid, since it is this strand which is aligned 3' to 5'. These conventions are followed in the nomenclature used herein. It should be noted, however, that in nature certain fingers, such as finger 4 of the protein GLI, bind to the+strand of nucleic acid: see Suzuki et al., (1994) NAR 22:3397-3405 and Pavletich and Pabo, (1993) Science 261:1701-1707. The incorporation of such fingers into DNA binding molecules according to the invention is envisaged.

The present invention may preferably be integrated with the rules set forth for zinc finger polypeptide engineering in our copending European or PCT patent applications having publication numbers WO98/53057, WO98/53060, WO98/53058, which describe improved techniques for designing zinc finger polypeptides capable of binding desired nucleic acid sequences. In combination with selection procedures, such as phage display, set forth for example in WO96/06166, these techniques enable the production of zinc finger polypeptides capable of recognising practically any desired sequence.

A zinc finger binding motif is a structure well known to those in the art and defined in, for example, Miller et al., (1985) EMBO J. 4:1609-1614; Berg (1988) PNAS (USA) 85:99-102; Lee et al., (1989) Science 245:635-637; see International patent applications WO96/06166 and WO96/32475, corresponding to U.S. Ser. No. 08/422,107, incorporated herein by reference.

In general, a preferred zinc finger framework has the structure:

(SEQ ID NO:34)
(A) $X_{0-2}$ C $X_{1-5}$ C $X_{9-14}$ H $X_{3-6}$ H/C where X is any amino acid, and the numbers in subscript indicate the possible numbers of residues represented by X.

In a preferred aspect of the present invention, zinc finger nucleic acid binding motifs may be represented as motifs having the following primary structure:

(SEQ ID NO:22)
(B) $X^a$ C $X_{2-4}$ C $X_{2-3}$ F $X^c$ X X X X L X X H X X $X^b$ H - linker The present invention is in one aspect concerned with the production of what are essentially engineered DNA binding proteins. In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the art. Moreover, any specific amino acid referred to herein may be wherein X (including $X^a$, $X^b$ and $X^c$) is any amino acid. $X_{2-4}$ and $X_{2-3}$ refer to the presence of 2 to 4, or 2 or 3, amino acids, respectively, and X X X X L X X H X X between Xc and Xb are designated positions −1, 1, 2,3,4,5,6,7,8, and 9. The Cys and His residues, which together co-ordinate the zinc metal atom, are marked in bold text and are usually invariant, as is the Leu residue at position +4 in the 60-helix.

Modifications to this representation may occur or be effected without necessarily abolishing zinc finger function, by insertion, mutation or deletion of amino acids. For example it is known that the second His residue may be replaced by Cys (Krizek et al., (1991) J. Am. Chem. Soc. 113:4518-4523) and that Leu at +4 can in some circumstances be replaced with Arg. The Phe residue before $X^c$ may be replaced by any aromatic other than Trp. Moreover, experiments have shown that departure from the preferred structure and residue assignments for the zinc finger are tolerated and may even prove beneficial in binding to certain nucleic acid sequences.

Preferably, $X^a$ is F/y–X or P–F/y–X. In this context, X is any amino acid. Preferably, in this context X is E, K, T or S. Less preferred but also envisaged are Q, V, A and P. The remaining amino acids remain possible.

Preferably, $X_{2-4}$ consists of two amino acids rather than four. The first of these amino acids may be any amino acid, but S, E, K, T, P and R are preferred. Advantageously, it is P or R. The second of these amino acids is preferably E, although any amino acid may be used.

Preferably, $X^b$ is T or I. Preferably, $X^c$ is S or T.

Preferably, $X_{2-3}$ is G-K-A, G-K-C, G-K-S or G-K-G. However, departures from the preferred residues are possible, for example in the form of M-R-N or M-R.

Preferably, the linker is T-G-E-K (SEQ ID NO: 23) or T-G-E-K-P (SEQ ID NO: 24).

As set out above, the major binding interactions occur with amino acids −1, +3 and +6. Amino acids +4 and +7 are largely invariant. The remaining amino acids may be essentially any amino acids. Preferably, position +9 is occupied by Arg or Lys. Advantageously, positions +1, +5 and +8 are not hydrophobic amino acids, that is to say are not Phe, Trp or Tyr. Preferably, position ++2 is any amino acid, and preferably serine, save where its nature is dictated by its role as a ++2 amino acid for an N-terminal zinc finger in the same nucleic acid binding molecule.

In a most preferred aspect, therefore, bringing together the above, the invention allows the definition of every residue in a zinc finger DNA binding motif which will bind specifically to a given target DNA triplet.

The code provided by the present invention is not entirely rigid; certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, therefore, the present invention provides a very large number of proteins which are capable of binding to every defined target DNA triplet.

Preferably, however, the number of possibilities may be significantly reduced. For example, the non-critical residues +1, +5 and +8 may be occupied by the residues Lys, Thr and Gln respectively as a default option. In the case of the other choices, for example, the first-given option may be employed as a default. Thus, the code according to the present invention allows the design of a single, defined polypeptide (a "default" polypeptide) which will bind to its target triplet.

Accordingly, the zinc fingers of the present invention can be prepared using a method comprising the steps of: (a) selecting a model zinc finger domain from the group consisting of naturally occurring zinc fingers and consensus zinc fingers; and (b) mutating at least one of positions −1, +3, +6 (and ++2) of the finger.

In general, naturally occurring zinc fingers may be selected from those fingers for which the DNA binding specificity is known. For example, these may be the fingers for which a crystal structure has been resolved: namely Zif268 (Elrod-Erickson et al., (1996) Structure 4:1171-1180), GLI (Pavletich and Pabo, (1993) Science 261:1701-1707), Tramtrack (Fairall et al., (1993) Nature 366:483-487) and YY1 (Houbaviy et al., (1996) PNAS (USA) 93:13577-13582).

Although mutation of the DNA-contacting amino acids of the DNA binding domain allows selection of polypeptides which bind to desired target nucleic acids, in a preferred embodiment residues which are outside the DNA-contacting region may be mutated. Mutations in such residues may affect the interaction between zinc fingers in a zinc finger polypeptide, and thus alter binding site specificity.

The naturally occurring zinc finger 2 in Zif268 makes an excellent starting point from which to engineer a zinc finger and is preferred.

Consensus zinc finger structures may be prepared by comparing the sequences of known zinc fingers, irrespective of whether their binding domain is known. Preferably, the consensus structure is selected from the group consisting of the consensus structure P Y K C P E C G K S F S Q K S D L V K H Q R T H T G (SEQ ID NO: 25), and the consensus structure P Y K C S E C G K A F S Q KS N L T R H Q R I H T G E K P (SEQ ID NO: 26).

The consensuses are derived from the consensus provided by Krizek et al., (1991) J. Am. Chem. Soc. 113: 4518-4523 and from Jacobs, (1993) PhD thesis, University of Cambridge, UK. In both cases, the linker sequences described above for joining two zinc finger motifs together, namely TGEK (SEQ ID NO: 23) or TGEKP (SEQ ID NO: 24) can be formed on the ends of the consensus. Thus, a P may be removed where necessary, or, in the case of the consensus terminating T G, E K (P) can be added.

The present invention provides methods of engineering and using zinc finger proteins in plants which zinc finger proteins are capable of binding to a target DNA sequence, and wherein binding to each base of the triplet by an α-helical zinc finger DNA binding motif in the polypeptide is determined as follows:

(a) if the 5' base in the triplet is G, then position +6 in the α-helix is Arg and/or position ++2 is Asp;

(b) if the 5' base in the triplet is A, then position +6 in the α-helix is Gln or Glu and ++2 is not Asp;

(c) if the 5' base in the triplet is T, then position +6 in the α-helix is Ser or Thr and position ++2 is Asp; or position +6 is a hydrophobic amino acid other than Ala;

(d) if the 5' base in the triplet is C, then position +6 in the α-helix may be any amino acid, provided that position ++2 in the α-helix is not Asp;

(e) if the central base in the triplet is G, then position +3 in the α-helix is His;

(f) if the central base in the triplet is A, then position +3 in the α-helix is Asn;

(g) if the central base in the triplet is T, then position +3 in the α-helix is Ala, Ser, Ile, Leu, Thr or Val; provided that if it is Ala, then one of the residues at −1 or +6 is a small residue;

(h) if the central base in the triplet is 5-meC, then position +3 in the α-helix is Ala, Ser, Ile, Leu, Thr or Val; provided that if it is Ala, then one of the residues at −1 or +6 is a small residue;

(i) if the 3' base in the triplet is G, then position −1 in the α-helix is Arg;

(j) if the 3' base in the triplet is A, then position −1 in the α-helix is Gln and position +2 is Ala;

(k) if the 3' base in the triplet is T, then position −1 in the α-helix is Asn; or position −1 is Gln and position +2 is Ser;

(l) if the 3' base in the triplet is C, then position −1 in the α-helix is Asp and Position +1 is Arg; where the central residue of a target triplet is C, the use of Asp at position +3 of a zinc finger polypeptide allows preferential binding to C over 5-meC.

The foregoing represents a set of rules which permits the design of a zinc finger binding protein specific for any given target DNA sequence.

When the nucleic acid specificity of the model finger selected is known, the mutation of the finger in order to modify its specificity to bind to the target DNA may be directed to residues known to affect binding to bases at which the natural and desired targets differ. Otherwise, mutation of the model fingers should be concentrated upon residues −1, +3, +6 and ++2 as provided for in the foregoing rules.

In order to produce a binding protein having improved binding, moreover, the rules provided by the present invention may be supplemented by physical or virtual modelling of the protein/DNA interface in order to assist in residue selection.

Methods for the production of libraries encoding randomised polypeptides are known in the art and may be applied in the present invention. Randomisation may be total, or partial; in the case of partial randomisation, the selected codons preferably encode options for amino acids as set forth in the rules above.

The invention encompasses library technology described in our copending International patent application WO98/53057, incorporated herein by reference in its entirety. WO98/53057 describes the production of zinc finger polypeptide libraries in which each individual zinc finger polypeptide comprises more than one, for example two or three, zinc fingers; and wherein within each polypeptide partial randomisation occurs in at least two zinc fingers.

This allows for the selection of the "overlap" specificity, wherein, within each triplet, the choice of residue for binding to the third nucleotide (read 3' to 5' on the+strand) is influenced by the residue present at position +2 on the subsequent zinc finger, which displays cross-strand specificity in binding. The selection of zinc finger polypeptides incorporating cross-strand specificity of adjacent zinc fingers enables the selection of nucleic acid binding proteins more quickly, and/or with a higher degree of specificity than is otherwise possible.

Zinc finger binding motifs engineered for use in accordance with the present invention may be combined into nucleic acid binding polypeptide molecules having a multiplicity of zinc fingers. Preferably, the proteins have at least two zinc fingers. In nature, zinc finger binding proteins commonly have at least three zinc fingers, although two-zinc finger proteins such as Tramtrack are known. The presence of at least three zinc fingers is preferred. Nucleic acid binding proteins may be constructed by joining the required fingers end to end, N-terminus to C-terminus. Preferably, this is effected by joining together the relevant nucleic acid sequences which encode the zinc fingers to produce a composite nucleic acid coding sequence encoding the entire binding protein.

A "leader" peptide may be added to the N-terminal finger. Preferably, the leader peptide is MAEEKP (SEQ ID NO: 27).

Zinc finger polypeptides comprising more than three zinc fingers, such as four, five, six, seven, eight or nine zinc fingers can also be used in conjunction with the present invention. Linkers that are preferably used to link zinc finger domains are described in co-pending patent applications GB 0013102.9, GB 0013103.7and GB 0013104.5 filed on May 30, 2000. An example of a multiple zinc finger protein described in this specification comprises zinc fingers 1-3 of TFIIIA and the three zinc fingers from Zif268 joined by zinc finger 4, including flanking sequences, of TFIIIA. We have called the zinc finger protein TFIIIAZif. Zinc finger 4 of TFIIIA does not bind DNA but acts as a linker in between the two sets of zinc fingers that are involved in DNA recognition. Despite the fact that this zinc finger does not make any base contacts within the major groove of the DNA, it is folded in the classical way, for Cys2His2 zinc fingers, around a Zn(II) ion and is folded to contain an alpha helix within its structure (Nolte et al., 1998). However, other linkers can be used in conjunction with the present invention to construct zinc finger proteins comprising multiple zinc finger domains.

B. Target Genes

Examples of target genes include any gene involved in any trait that may be of interest to a farmer or grower, a processor, or a consumer of a plant or plant product.

For example, genes involved in the starch characteristics are useful target genes and the present invention can be used in conjunction with starch branching enzyme (for example) to generate corn plants which generate seed with super-branching starch.

Genes involved in oil characteristics are useful target genes and the present invention can be used in conjunction with delta-12-desaturase (for example) to generate corn plants which generate seed with higher oleic and lower linoleic acid.

Genes involved in cotton fiber characteristics are useful target genes and the technology of the present invention can be used to modify the expression of such genes to improve traits such as fiber strength.

A further example is provided by the genes involved in the biosynthesis and catabolism of gibberellins. The gibberellins are a class of plant hormones involved in the determination of many plant traits including elongation growth, bolting/flowering, leaf expansion, seed set, fruit size and dormancy. Accordingly, the regulation of genes involved in the biosynthesis and catabolism of gibberellins can be used to generate plants such as wheat, corn, sugar beet and sugar cane with improved traits (Phillips et al. (1995) Plant Physiol. 108:1049-1057; MacMillin et al. (1997) Plant Physiol. 113:1369-1377; Williams et al. (1998) Plant Physiol. 117:559-563; and Thomas et al. (1999) Proc. Natl. Acad. Sci. USA 96:4698-4703).

Genes involved in nitrogen metabolism (for example glutamine synthetase, asparagine synthetase, GOGAT, glutamate dehydrogenase) are useful target genes and the technology of the present invention can be used to modify the expression of such genes to improve nitrogen use efficiency in plants and thereby to reduce the requirement for the application of inorganic fertilizers.

Genes involved in the biosynthesis of plant cell components such as cellulose and lignin can be targeted by the technology of the present invention to modify digestibility in crops such as corn which are used as silage.

Genes whose products are responsible for ripening (such as polygalacturonase and ACC oxidase) are interesting target genes as the present invention can be used to modify ripening characteristics in plants such as tomato, avocado, and banana.

Genes involved in the biosynthesis of volatile esters, which are important flavor compounds in fruits and vegetables, are equally interesting target genes and the present invention can be used to improve such traits (Dudavera et al.

(1996) Plant Cell 8:1137-1148; Dudavera et al. (1998) Plant J. 14:297-304; Ross et al. (1999) Arch. Biochem. Biophys. 367:9-16).

Genes which are involved in the biosynthesis of plant-derived pharmaceutically important compounds are also potential target gene. Using the technology of the present invention, the up-regulation of a rate-limiting step in the biosynthetic pathway of a pharmaceutically important compound will result in the production of higher levels of such compound in the plant.

Additionally, target genes used in conjunction with the present invention include genes encoding allergens such as the peanut allergens Arah1, Arah2 and Arah3. Rabjohn et al. J. Clin. Invest. 103:535-542. Down-regulation of such genes using the technology of the present invention is expected to reduce the allergenicity of the transgenic peanuts.

Examples of heterologous target genes include genes which are introduced into a plant for the production of biodegradable plastic (for example) but which are placed under the regulatory control of a zinc finger protein of the present invention.

C. Target DNA Sequence

Most commonly, target DNA sequences will be sequences associated with a target gene that is to be regulated by a zinc finger protein of the present invention. Target DNA sequences include note only sequences which are naturally associated with target genes, but also other sequences which can be configured with a gene of interest to allow the up- or down regulation of such a gene of interest. For example, the known binding site of a given zinc finger protein can be a target sequence and, when operably linked to a gene of interest, will allow the gene of interest to be regulated by the given zinc finger protein.

D. DNA Libraries

DNA sequences for use in screening methods to select zinc fingers and corresponding DNA sequences can be provided as a library of related sequences having homology to one another (as opposed to a genomic library, for example, obtained by cutting up a large amount of essentially unrelated sequences).

A library of DNA sequences can be used in at least two different ways. First, it can be used in a screen to identify zinc fingers that bind to a specific sequence. Second, it can be used to confirm the specificity of selected zinc fingers.

A DNA library is advantageously used to test the selectivity of a zinc finger for nucleotide sequences of length N. Consequently, since there are four different nucleotides that occur naturally in genomic DNA, the total number of sequences required to represent all possible base permutations for a sequence of length N is $4^N$. N is an integer having a value of at least three. That it to say that the smallest library envisaged for testing binding to a nucleotide sequence where only one DNA triplet is varied, consists of 64 different sequences. However, N can be any integer greater than or equal to 3 such as 4, 5, 6, 7, 8 or 9. Typically, N only needs to be three times the number of zinc fingers being tested, optionally included a few additional residues outside of the binding site that can influence specificity. Thus, by way of example, to test the specificity of a protein comprising three zinc fingers, where all three fingers have been engineered, it can be desirable to use a library where N is at least 9.

Libraries of DNA sequences can be screened using a number of different methods. For example, the DNA can be immobilised to beads and incubated with zinc fingers that are labelled with an affinity ligand such as biotin or expressed on the surface of phage. Complexes between the DNA and zinc finger can be selected by washing the beads to remove unbound zinc fingers and then purifying the beads using the affinity ligand bound to the zinc fingers to remove beads that do not contain bound zinc fingers. Any remaining beads should contain DNA/zinc finger complexes. Individual beads can be selected and the identity of the DNA and zinc finger determined. Other modifications to the technique include the use of detectable labels, for example fluorescently labelling the zinc fingers and sorting beads that have zinc fingers bound to them by FACS.

In an alternative method, the DNA sequences in the library are immobilised at discrete positions on a solid substrate, such as a DNA chip, such that each different sequence is separated from other sequences on the solid substrate. Binding of zinc finger proteins is determined as described below and individual proteins isolated (which can be conveniently achieved by the use of phage display techniques). This technique can also be used as a second step after a zinc finger has been selected by, for example, the bead method described above, to characterise fully the binding specificity of a selected zinc finger In a DNA library, it is generally not necessary or desirable for all positions to be randomised. Preferably only a subsequence of N bases of the complete DNA sequence is varied. The $4^N$ possible permutations of the DNA sequence of length N sequence are typically arranged in 4N sub-libraries, wherein for any one sub-library one base in the DNA sequence of length N is defined and the other N-1 bases are randomised. Thus in the case of a varied DNA triplet, there will be 12 sub-libraries.

As mentioned above, the nucleotide sequence of length N is generally part of a longer DNA molecule. However, the nucleotide sequence of length N typically occupies the same position within the longer molecule in each of the varied sequences even though the sequence of N itself can vary. The other sequences within the DNA molecule are generally the same throughout the library. Thus the library can be said to consist of a library of $4^N$ DNA molecules of the formula $R^1$-(A/C/G/T)$_4^N$-$R^2$, wherein $R^1$ and $R^2$ can be any nucleotide sequence.

Preferably, each sequence is also represented as a dilution/concentration series. Thus the immobilized DNA library can occupy $Z4^N$ discrete positions on the chip where Z is the number of different dilutions in the series and is an integer having a value of at least 2. The range of DNA concentrations for the dilution series is typically in the order of 0.01 to 100 pmol cm$^{-2}$, preferably from 0.05 to 5 pmol cm$^{-2}$. The concentrations typically vary 10-fold, i.e. a series can consist of 0.01, 0.1, 1, 10 and 100 pmol cm$^{-2}$, but can vary, for example, by 2- or 5-fold.

The advantage of including the DNA sequences in a dilution series is that it is then possible to estimate $K_d$S for protein/DNA complexes using standard techniques such as the Kaleidagraph™ version 2.0 program (Abelback Software).

The DNA molecules in the library are at least partially double-stranded, in particular at least the nucleotide sequence of length N is double-stranded. Single stranded regions can be included, for example to assist in attaching the DNA library to the solid substrate.

Techniques for producing immobilized libraries of DNA molecules have been described in the art. Generally, most prior art methods described how to synthesize single-stranded nucleic acid molecule libraries, using for example masking techniques to build up various permutations of sequences at the various discrete positions on the solid substrate. U.S. Pat. No. 5,837,832 (the '832 patent), describes an improved method for producing DNA arrays immobilized to silicon substrates based on very large scale integration technology. In particular, the '832 patent describes a strategy called "tiling" to synthesize specific sets of probes at spatially-defined locations on a substrate which can be used to produced the immobilized DNA libraries of the present invention. The '832 patent also provides references for earlier techniques that can also be used.

However, an important aspect of the present invention is that it relates to DNA binding proteins, zinc fingers that bind double-stranded DNA. Thus single-stranded nucleic acid molecule libraries using the prior art techniques referred to above will then need to be converted to double-stranded DNA libraries by synthesizing a complementary strand. An example of the conversion of single-stranded nucleic acid molecule libraries to double-stranded DNA libraries is given in Bulyk et al. (1999) Nature Biotechnol. 17:573-577. The technique described in Bulyk et al. (1999) typically requires the inclusion of a constant sequence in every member of the library (i.e. within $R^1$ or $R^2$ in the generic formula given above) to which a nucleotide primer is bound to act as a primer for second strand synthesis using a DNA polymerase and other appropriate reagents. If required, deoxynucleotide triphosphates (dNTPs) having a detectable labeled can be included to allow the efficiency of second strand synthesis to be monitored. Also the detectable label can assist in detecting binding of zinc fingers when the immobilized DNA library is in use.

Alternatively, double-stranded molecules can be synthesized off the solid substrate and each pre-formed sequence applied to a discrete position on the solid substrate. An example of such a method is to synthesis palindromic single-stranded nucleic acids. See U.S. Pat. No. 5,556,752.

Thus DNA can typically be synthesized in situ on the surface of the substrate. However, DNA can also be printed directly onto the substrate using for example robotic devices equipped with either pins or piezo electric devices.

The library sequences are typically immobilized onto or in discrete regions of a solid substrate. The substrate can be porous to allow immobilization within the substrate or substantially non-porous, in which case the library sequences are typically immobilized on the surface of the substrate. The solid substrate can be made of any material to which polypeptides can bind, either directly or indirectly. Examples of suitable solid substrates include flat glass, silicon wafers, mica, ceramics and organic polymers such as plastics, including polystyrene and polymethacrylate. It can also be possible to use semi-permeable membranes such as nitrocellulose or nylon membranes, which are widely available. The semi-permeable membranes can be mounted on a more robust solid surface such as glass. The surfaces can optionally be coated with a layer of metal, such as gold, platinum or other transition metal. A particular example of a suitable solid substrate is the commercially available BiaCore™ chip (Pharmacia Biosensors).

Preferably, the solid substrate is generally a material having a rigid or semi-rigid surface. In preferred embodiments, at least one surface of the substrate will be substantially flat, although in some embodiments it can be desirable to physically separate synthesis regions for different polymers with, for example, raised regions or etched trenches. Preferably the solid substrate is not a microtiter plate or bead. It is also preferred that the solid substrate is suitable for the high density application of DNA sequences in discrete areas of typically from 50 to 100 μm, giving a density of 10000 to 40000 $cm^{-2}$.

The solid substrate is conveniently divided up into sections. This can be achieved by techniques such as photoetching, or by the application of hydrophobic inks, for example Teflon-based inks (Cel-line, USA).

Discrete positions, in which each different member of the library is located can have any convenient shape, e.g., circular, rectangular, elliptical, wedge-shaped, etc.

Attachment of the library sequences to the substrate can be by covalent or non-covalent means. The library sequences can be attached to the substrate via a layer of molecules to which the library sequences bind. For example, the library sequences can be labeled with biotin and the substrate coated with avidin and/or streptavidin. A convenient feature of using biotinylated library sequences is that the efficiency of coupling to the solid substrate can be determined easily. Since the library sequences can bind only poorly to some solid substrates, it is often necessary to provide a chemical interface between the solid substrate (such as in the case of glass) and the library sequences.

Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO98/49557.

Binding of zinc fingers to the immobilized DNA library can be determined by a variety of means such as changes in the optical characteristics of the bound DNA (i.e. by the use of ethidium bromide) or by the use of labeled zinc finger polypeptides, such as epitope tagged zinc finger polypeptides or zinc finger polypeptides labeled with fluorophores such as green fluorescent protein (GFP). Other detection techniques that do not require the use of labels include optical techniques such as optoacoustics, reflectometry, ellipsometry and surface plasma resonance (SPR). See, WO97/49989.

Binding of epitope tagged zinc finger polypeptides is typically assessed by immunological detection techniques where the primary or secondary antibody comprises a detectable label. A preferred detectable label is one that emits light, such as a fluorophore, for example phycoerythrin.

The complete DNA library is typically read at the same time by charged coupled device (CCD) camera or confocal imaging system. Alternatively, the DNA library can be placed for detection in a suitable apparatus that can move in an X-Y direction, such as a plate reader. In this way, the change in characteristics for each discrete position can be measured automatically by computer controlled movement of the array to place each discrete element in turn in line with the detection means.

E. Nucleic Acid Vectors Encoding Zinc Finger Proteins

Polynucleotides encoding zinc finger proteins for use in the invention can be incorporated into a recombinant replicable vector. The vector can be used to replicate the nucleic acid in a compatible host cell and the vector can be recovered from the host cell. Suitable host cells include bacteria such as *Escherichia coli*, yeast and eukaryotic cell lines.

Preferably, a polynucleotide encoding a zinc finger protein according to the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences can be modified, for example by the addition of further transcriptional regulatory elements to make the level of transcription directed by the control sequences more responsive to transcriptional modulators.

Vectors of the invention can be transformed or transfected into a suitable host cell as described below to provide for expression of a protein of the invention.

The vectors can be for example, plasmid or virus vectors provided with an origin of replication, optionally a promoter for the expression of the said polynucleotide and optionally a regulator of the promoter. The vectors can contain one or more selectable marker genes and these will vary depending on the system used, but are known to those of skill in the art. Vectors can be used, for example, to transfect or transform a host cell.

Control sequences operably linked to sequences encoding the protein of the invention include promoters/enhancers and other expression regulation signals such as terminators. These control sequences can be selected to be compatible with the host cell in which the expression vector is designed to be used. The term promoter is well-known in the art and encompasses nucleic acid regions ranging in size and complexity from minimal promoters to promoters including upstream elements and enhancers.

The promoter is typically selected from promoters which are functional in plant cells, although prokaryotic promoters and promoters functional in other eukaryotic cells can be used. Typically, the promoter is derived from viral or plant gene sequences. For example, the promoter can be derived from the genome of a cell in which expression is to occur. With respect to plant promoters, they can be promoters that function in a ubiquitous manner or, alternatively, a tissue-specific manner. Tissue-specific promoters specific for different tissues of the plant are particularly preferred. Examples are provided below. Tissue-specific expression can be used to confine expression of the binding domain and/or binding partner to a cell type or tissue/organ of interest. Promoters can also be used that respond to specific stimuli, for example promoters that are responsive to plant hormones. Viral promoters can also be used, for example the CaMV 35S promoter well known in the art.

It can also be advantageous for the promoters to be inducible so that the levels of expression of the heterologous gene can be regulated during the life-time of the cell. Inducible means that the levels of expression obtained using the promoter can be regulated. Inducible expression allows the researcher to control when expression of the polypeptides takes place.

In addition, any of these promoters can be modified by the addition of further regulatory sequences, for example enhancer sequences. Chimeric promoters can also be used comprising sequence elements from two or more different promoters described above.

Advantageously, a plant expression vector encoding a zinc finger protein according to the invention can comprise a locus control region (LCR). LCRs are capable of directing high-level integration site independent expression of transgenes integrated into host cell chromatin (Stief et al. (1989) Nature 341:343); Lang et al. (1991) Nucl. Acids Res. 19:5851-5856.).

According to the invention, the zinc finger protein constructs of the invention are expressed in plant cells under the control of transcriptional regulatory sequences that are known to function in plants. The regulatory sequences selected will depend on the required temporal and spatial expression pattern of the zinc finger protein in the host plant. Many plant promoters have been characterized and would be suitable for use in conjunction with the invention. By way of illustration, some examples are provided below:

A large number of promoters are known in the art which direct expression in specific tissues and organs (e.g. roots, leaves, flowers) or in cell types (e.g. leaf epidermal cells, leaf mesophyll cells, root cortex cells). For example, the maize PEPC promoter from the phosphoenol carboxylase gene (Hudspeth and Grula (1989) Plant Mol. Biol. 12:579-589) is green tissue-specific; the trpA gene promoter is pith cell-specific (WO93/07278 to Ciba-Geigy); the TA29 promoter is pollen-specific. Mariani et al. (1990) Nature 347: 737-741; and Mariani et al. (1992) Nature 357:384-387.

Other promoters direct transcription under conditions of presence of light or absence or light or in a circadian manner. For example, the GS2 promoter described by Edwards and Coruzzi (1989) Plant Cell 1:241-248 is induced by light, whereas the AS1 promoter described by Tsai and Coruzzi (1990) EMBO J. 9:323-332 is expressed only in conditions of darkness.

Other promoters are wound-inducible and typically direct transcription not just on wound induction, but also at the sites of pathogen infection. Examples are described by Xu et al. (1993) Plant Mol. Biol. 22:573-588; Logemann et al. (1989) Plant Cell 1:151-158; and Firek et al. (1993) Plant Mol. Biol. 22:129-142.

Further plant promoters of interest are the bronze promoter (Ralston et al. (1988) Genetics 119:185-197 and Genbank Accession No. X07937.1) which directs expression of UDPglucose flavanoid glycosyl-transferase in maize, the patatin-1 gene promoter (Jefferson et al. (1990) Plant Mol. Biol. 14:995-1006) that contains sequences capable of directing tuber-specific expression, and the phenylalanine ammonia lyase promoter (Bevan et al. (1989) EMBO J. 8:1899-1906) though to be involved in responses to mechanical wounding and normal development of the xylem and flower.

A number of constitutive promoters can be used in plants. These include the Cauliflower Mosaic Virus (CaMV) 35S promoter (U.S. Pat. No. 5,352,605 and U.S. Pat. No. 5,322, 938, both to Monsanto) including minimal promoters (such as the −90 CaMV 35S promoter) linked to other regulatory sequences, the rice actin promoter (McElroy et al. (1991) Mol. Gen. Genet. 231:150-160), and the maize and sunflower ubiquitin promoters. Christensen et al. (1989) Plant Mol. Biol. 12:619-632; and Binet et al. (1991) Plant Science 79:87-94).

A further promoter of interest is the inducible promoter described by Aoyama and Chua (1997) Plant J. 11:605-612; and Zou and Chua (2000) Curr. Op. Biotech. 11:146-151. By using this inducible promoter system, transgenic lines can be established which carry the zinc finger chimera but express it only after addition of an inducer. Thus the zinc fingers of the present invention can be expressed in response to the inducer allowing the dose or level of zinc finger protein in the cell or plant to the adjusted to a desired amount.

Using promoters that direct transcription in the plant species of interest, the zinc finger protein of the invention can be expressed in the required cell or tissue types. For example, if it is the intention to utilize the zinc finger protein to regulate a gene in a specific cell or tissue type, then the appropriate promoter can be used to direct expression of the zinc finger protein construct.

An appropriate terminator of transcription is fused downstream of the selected zinc finger protein containing transgene and any of a number of available terminators can be used in conjunction with the invention. Examples of transcriptional terminator sequences that are known to function in plants include the nopaline synthase terminator found in the pBI vectors (Clontech catalog 1993/1994), the E9 terminator from the rbcS gene, and the tm1 terminator from CaMV.

A number of sequences found within the transcriptional unit are known to enhance gene expression and these can be used within the context of the current invention. Such sequences include intron sequences which, particularly in monocotyledonous cells, are known to enhance expression. Both intron 1 of the maize Adh1 gene and the intron from the maize bronze1 gene have been found to be effective in enhancing expression in maize cells (Callis et al. (1987) Genes Develop. 1:1183-1200) and intron sequences are frequently incorporated into plant transformation vectors, typically within the non-translated leader.

A number of virus-derived non-translated leader sequences have been found to enhance expression, especially in dicotyledonous cells. Examples include the "Ω" leader sequence of Tobacco Mosaic Virus, and similar leader sequences of Maize Chlorotic Mottle Virus and Alfalfa Mosaic Virus. Gallie et al. (1987) Nucl. Acids Res. 15:8693-8711; and Shuzeski et al. (1990) Plant Mol. Biol. 15:65-79.

The zinc finger proteins of the current invention are targeted to the cell nucleus so that they are able to interact with host cell DNA and bind to the appropriate DNA target in the nucleus and regulate transcription. To effect this, a Nuclear Localization Sequence (NLS) is incorporated in frame with the expressible zinc finger construct. The NLS can be fused either 5' or 3' to the zinc finger encoding sequence.

The NLS of the wild-type Simian Virus 40 Large T-Antigen (Kalderon et al. (1984) Cell 37:801-813; and Markland et al. (1987) Mol. Cell. Biol. 7:4255-4265) is an appropriate NLS and has previously been shown to provide an effective nuclear localization mechanism in plants. van der Krol et al. (1991) Plant Cell 3:667-675. However, several alternative NLSs are known in the art and can be used instead of the SV40 NLS sequence. These include the Nuclear Localization Signals of TGA-1A and TGA-1B (van der Krol et al. (1991)).

A variety of transformation vectors are available for plant transformation and the zinc finger protein encoding genes of the invention can be used in conjunction with any such vectors. The selection of vector will depend on the preferred transformation technique and the plant species that is to be transformed. For certain target species, different selectable markers can be preferred.

For *Agrobacterium*-mediated transformation, binary vectors or vectors carrying at least one T-DNA border sequence are suitable. A number of vectors are available including pBIN19 (Bevan (1984) Nucl. Acids Res. 12:8711-8721), the pBI series of vectors, and pCIB10 and derivatives thereof. Rothstein et al. (1987) Gene 53:153-161; and WO95/33818.

Binary vector constructs prepared for *Agrobacterium* transformation are introduced into an appropriate strain of *Agrobacterium tumefaciens* (for example, LBA 4044 or GV 3101) either by triparental mating or direct transformation. Bevan (1984); and Höfgen and Willmitzer, Nucl. Acids Res. 16:9877 (1988).

For transformation which is not *Agrobacterium*-mediated (i.e. direct gene transfer), any vector is suitable and linear DNA containing only the construct of interest can be preferred. Direct gene transfer can be undertaken using a single DNA species or multiple DNA species (cotransformation; Schroder et al. (1986) Biotechnol. 4:1093-1096).

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing DNA binding protein expression and function are known to those skilled in the art. Gene presence, amplification and/or expression can be measured in a sample directly, for example, by conventional Southern blotting, Northern blotting to quantitate the transcription of mRNA, dot blotting (DNA or RNA analysis), or in situ hybridization, using an appropriately labeled probe which can be based on a sequence provided herein. Those skilled in the art will readily envisage how these methods can be modified, if desired.

DNA can be stably incorporated into cells or can be transiently expressed using methods known in the art. Stably transfected cells can be prepared by transfecting cells with an expression vector having a selectable marker gene, and growing the transfected cells under conditions selective for cells expressing the marker gene. To prepare transient transfectants, cells are transfected with a reporter gene to monitor transfection efficiency.

Heterologous DNA can be introduced into plant host cells by any method known in the art, such as electroporation or *A. tumefaciens* mediated transfer. Although specific protocols can vary from species to species, transformation techniques are well known in the art for most commercial plant species.

In the case of dicotyledonous species, *Agrobacterium*-mediated transformation is generally a preferred technique as it has broad application to many dicotyledons species and is generally very efficient. *Agrobacterium*-mediated transformation generally involves the co-cultivation of *Agrobacterium* with explants from the plant and follows procedures and protocols that are known in the art. Transformed tissue is generally regenerated on medium carrying the appropriate selectable marker. Protocols are known in the art for many dicotyledonous crops including (for example) cotton, tomato, canola and oilseed rape, poplar, potato, sunflower, tobacco and soybean (see for example EP 0 317 511, EP 0 249 432, WO87/07299, U.S. Pat. No. 5,795,855).

In addition to *Agrobacterium*-mediated transformation, various other techniques can be applied to dicotyledons. These include polyethylene glycol (PEG) and electroporation-mediated transformation of protoplasts, and microinjection. Potrykus et al. (1985) Mol. Gen. Genet. 199:169-177; Reich et al. (1986) Biotechnol. 4:1001-1004; Klein et al. (1987) Nature 327:70-73. As with *Agrobacterium*-mediated transformation, transformed tissue is generally regenerated on medium carrying the appropriate selectable marker using standard techniques known in the art.

Although *Agrobacterium*-mediated transformation has been applied successfully to monocotyledonous species such as rice and maize and protocols for these approaches are available in the art, the most widely used transformation techniques for monocotyledons remain particle bombardment, and PEG and electroporation-mediated transformation of protoplasts.

In the case of maize, techniques are available for transformation using particle bombardment. Gordon-Kamm et al. (1990) Plant Cell 2:603-618; Fromm et al. (1990) Biotechnol. 8:833-839; and Koziel et al. (1993) Biotechnol. 11:194-200. The preferred method is the use of biolistics using, for instance, gold or tungsten. Suitable methods are known in the art and described, for instance, in U.S. Pat. Nos. 5,489,520 and 5,550,318. See also, Potrykus (1990) Bio/Technol. 8:535-542; and Finnegan et al. (1994) Bio/Technol. 12:883-888.

In the case of rice, protoplast-mediated transformation for both Japonica- and Indica-types has been described (Zhang et al. (1988) Plant Cell Rep. 7:379-384; Shimamoto et al. Nature 338:274-277; Datta et al. (1990) Biotechnol. 8:736-740) and both types are also routinely transformable using particle bombardment. Christou et al. (1991) Biotechnol. 9:957-962.

In the case of wheat, transformation by particle bombardment has been described for both type C long-term regenerable callus (Vasil et al. (1992) Biotechnol. 10:667-674) and immature embryos and immature embryo-derived callus (Vasil et al. (1993) Biotechnol. 11:1553-1558; Weeks et al. (1993) Plant Physiol. 102:1077-1084). A further technique is described in published patent applications WO94/13822 and WO95/33818.

Transformation of plant cells is normally undertaken with a selectable marker that can provide resistance to an antibiotic or to a herbicide. Selectable markers that are routinely used in transformation include the nptII gene which confers resistance to kanamycin (Messing & Vierra (1982) Gene 19:259-268; and Bevan et al. (1983) Nature 304:184-187), the bar gene which confers resistance to the herbicide phosphinothricin (White et al. (1990) Nucl. Acids Res. 18:1062; Spencer et al. (1990) Theor. Appl. Genet. 79:625-631), the hph gene which confers resistance to the antibiotic hygromycin (Blochlinger and Diggelmann (1984) Mol. Cell. Biol. 4:2929-2931), and the dhfr gene which confers resistance to methotrexate (Bourouis et al. (1983) EMBO J. 2:1099-1104). More recently, a number of selection systems have been developed which do not rely of selection for resistance to antibiotic or herbicide. These include the inducible isopentyl transferase system described by Kunkel et al. (1999) Nature Biotechnol. 17:916-919.

The zinc finger protein constructs of the invention are suitable for expression in a variety of different organisms. However, to enhance the efficiency of expression it can be necessary to modify the nucleotide sequence encoding the zinc finger protein to account for different frequencies of codon usage in different host organisms. Hence it is preferable that the sequences to be introduced into organisms, such as plants, conform to preferred usage of codons in the host organism.

In general, high expression in plants is best achieved from codon sequences that have a GC content of at least 35% and preferably more than 45%. This is thought to be because the existence of ATTTA motifs destabilize messenger RNAs and the existence of AATAAA motifs can cause inappropriate polyadenylation, resulting in truncation of transcription. Murray et al. (1989) (Nucl. Acids Res. 17:477-498) have shown that even within plants, monocotyledonous and dicotyledonous species have differing preferences for codon usage, with monocotyledonous species generally preferring GC richer sequences. Thus, in order to achieve optimal high level expression in plants, gene sequences can be altered to accommodate such preferences in codon usage in such a manner that the codons encoded by the DNA are not changed.

Plants also have a preference for certain nucleotides adjacent to the ATG encoding the initiating methionine and for most efficient translation, these nucleotides can be modified. To facilitate translation in plant cells, it is preferable to insert, immediately upstream of the ATG representing the initiating methionine of the gene to be expressed, a "plant translational initiation context sequence". A variety of sequences can be inserted at this position. These include the sequence the sequence 5'-AAGGAGATATAACAATG-3' (SEQ ID NO: 1) (Prasher et al. (1992) Gene 111:229-233; and Chalfie et al. (1992) Science 263:802-805), the sequence 5'-GTCGACCATG-3' (SEQ ID NO: 2) (Clontech 1993/1994 catalog, page 210), and the sequence 5'-TAAACAATG-3'. Joshi et al. (1987) Nucl. Acids Res. 15:6643-6653. For any particular plant species, a survey of natural sequences available in any databank (e.g. GenBank) can be undertaken to determine preferred "plant translational initiation context sequences" on a species-by-species basis.

Any changes that are made to the coding sequence can be made using techniques that are well known in the art and include site directed mutagenesis, PCR, and synthetic gene construction. Such methods are described in published patent applications EP 0 385 962, EP 0 359 472 and WO93/07278. Well-known protocols for transient expression in plants can be used to check the expression of modified genes before their transfer to plants by transformation.

F. Regulation of Gene Expression In Vivo in Plants Using Zinc Fingers

The present invention provides a method of regulating gene expression in a plant using an engineered zinc finger.

Thus, zinc fingers such as those designed or selected as described above are useful in switching or modulating gene expression in plants, in particular with respect to agricultural biotechnology applications as described below.

A fusion polypeptide comprising a zinc finger targeting domain and a DNA cleavage domain can be used to regulate gene expressing by specific cleavage of nucleic acid sequence. More usually, the zinc fingers will be fused to a transcriptional effector domain to activate or repress transcription from a gene that possesses the zinc finger binding sequence in its upstream sequences. Zinc fingers capable of differentiating between U and T can be used to preferentially target RNA or DNA, as required.

Thus zinc finger polypeptides according to the invention will typically require the presence of a transcriptional effector domain, such as an activation domain or a repressor domain. Examples of transcriptional activation domains include the VP 16 and VP64 transactivation domains of Herpes Simplex Virus. Alternative transactivation domains are various and include the maize C1 transactivation domain sequence (Sainz et al. (1997) Mol. Cell. Biol. 17:115-22) and P1 (Goff et al. (1992) Genes Dev. 6:864-75; and Estruch et al. (1994) Nucl. Acids Res. 22:3983-89) and a number of other domains that have been reported from plants. Estruch et al. (1994).

Instead of incorporating a transactivator of gene expression, a repressor of gene expression can be fused to the Zinc finger protein and used to down regulate the expression of a gene contiguous or incorporating the zinc finger protein target sequence. Such repressors are known in the art and include, for example, the KRAB-A domain (Moosmann et al. (1997) Biol. Chem. 378:669-677) the engrailed domain (Han et al. (1993) EMBO J. 12:2723-2733) and the snag domain (Grimes et al. (1996) Mol. Cell. Biol. 16:6263-6272). These can be used alone or in combination to down-regulate gene expression.

Another possible application discussed above is the use of zinc fingers fused to nucleic acid cleavage moieties, such as the catalytic domain of a restriction enzyme, to produce a restriction enzyme capable of cleaving only target DNA of a specific sequence. Kim et al. (1996) Proc. Natl. Acad. Sci. USA 93:1156-1160. Using such approaches, different zinc finger domains can be used to create restriction enzymes with any desired recognition nucleotide sequence. Preferably, the expression of these zinc finger-enzyme fusion proteins is inducible. Enzymes other than those that cleave nucleic acids can also be used for a variety of purposes.

The target gene can be endogenous or heterologous to the genome of the cell, for example fused to a heterologous coding sequence. However, in either case it will comprise a target DNA sequence, such as a target DNA sequence described above, to which a zinc finger according to the invention binds. The zinc finger is typically expressed from a DNA construct present in the host cell comprising the target sequence. The DNA construct is preferably stably integrated into the genome of the host cell, but this is not essential.

Thus a host plant cell according to the invention comprises a target DNA sequence and a construct capable of directing expression of the zinc finger molecule in the cell.

Suitable constructs for expressing the zinc finger molecule are known in the art and are described in section E above. The coding sequence can be expressed constitutively or be regulated. Expression can be ubiquitous or tissue-specific. Suitable regulatory sequences are known in the art and are also described in section E above. Thus the DNA construct will comprise a nucleic acid sequence encoding a zinc finger operably linked to a regulatory sequence capable of directing expression of the zinc finger molecule in a host cell.

It can also be desirable to use target DNA sequences that include operably linked neighboring sequences that bind transcriptional regulatory proteins, such as transactivators. Preferably the transcriptional regulatory proteins are endogenous to the cell. If not, they will typically need to be introduced into the host cell using suitable nucleic acid constructs.

Techniques for introducing nucleic acid constructs into plant cells are known in the art and many are described both in section E and below in the section on the production of transgenic plants.

"Transgenic" in the present context denotes organisms and more especially plants in which one or more cells receive a recombinant DNA molecule. Typically the transgene introduced will be transferred to the next generation which is also thus denoted "transgenic".

The information introduced into the organism is preferably a species foreign to the recipient animal (i.e., "heterologous"), but the information can also be foreign only to the particular individual recipient, or genetic information already possessed by the recipient. In the last case, the introduced gene can be differently expressed than is the native gene.

"Operably linked" refers to polynucleotide sequences that are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and a transcription termination sequence. The term "control sequences" is intended to include, at a minimum, components whose presence can influence expression, and can also include additional components whose presence is advantageous, for example, leader sequences and fusion partner sequences.

Thus, a polynucleotide construct for use in the present invention, to introduce a nucleotide sequence encoding a zinc finger molecule into the genome of a multicellular organism, typically comprises a nucleotide sequence encoding the zinc finger molecule operably linked to a regulatory sequence capable of directing expression of the coding sequence. In addition the polynucleotide construct can comprise flanking sequences homologous to the host cell organism genome to aid in integration.

G. Construction of Transgenic Plants Expressing Zinc Finger Molecules

A transgenic plant of the invention can be produced from any plant such as the seed-bearing plants (angiosperms), and conifers. Angiosperms include dicotyledons and monocotyledons. Examples of dicotyledonous plants include tobacco, (*Nicotiana plumbaginifolia* and *Nicotiana tabacum*), arabidopsis (*Arabidopsis thaliana*), Brassica napus, Brassica nigra, Datura innoxia, Vicia narbonensis, Vicia faba, pea (*Pisum sativum*), cauliflower, carnation and lentil (*Lens culinaris*). Examples of monocotyledonous plants include cereals such as wheat, barley, oats and maize.

Techniques for producing transgenic plants are well known in the art. Typically, either whole plants, cells or protoplasts can be transformed with a suitable nucleic acid construct encoding a zinc finger molecule or target DNA (see above for examples of nucleic acid constructs). There are many methods for introducing transforming DNA constructs into cells, but not all are suitable for delivering DNA to plant cells. Suitable methods include *Agrobacterium* infection (see, among others, Turpen et al. (1993) J. Virol. Met. 42:227-239) or direct delivery of DNA such as, for example, by PEG-mediated transformation, by electroporation or by acceleration of DNA coated particles. Acceleration methods are generally preferred and include, for example, microprojectile bombardment. A typical protocol for producing transgenic plants (in particular monocotyledons), taken from U.S. Pat. No. 5,874,265, is described below.

An example of a method for delivering transforming DNA segments to plant cells is microprojectile bombardment. In this method, non-biological particles can be coated with nucleic acids and delivered into cells by a propelling force. Exemplary particles include those comprised of tungsten, gold, platinum, and the like.

A particular advantage of microprojectile bombardment, in addition to it being an effective means of reproducibly stably transforming both dicotyledons and monocotyledons, is that neither the isolation of protoplasts nor the susceptibility to *Agrobacterium* infection is required. An illustrative embodiment of a method for delivering DNA into plant cells by acceleration is a Biolistics Particle Delivery System, that can be used to propel particles coated with DNA through a screen, such as a stainless steel or Nytex screen, onto a filter surface covered with plant cells cultured in suspension. The screen disperses the tungsten-DNA particles so that they are not delivered to the recipient cells in large aggregates. It is believed that without a screen intervening between the projectile apparatus and the cells to be bombarded, the projectiles aggregate and can be too large for attaining a high frequency of transformation. This can be due to damage inflicted on the recipient cells by projectiles that are too large.

For the bombardment, cells in suspension are preferably concentrated on filters. Filters containing the cells to be bombarded are positioned at an appropriate distance below the macroprojectile stopping plate. If desired, one or more screens are also positioned between the gun and the cells to be bombarded. Through the use of techniques set forth herein one can obtain up to 1000 or more clusters of cells transiently expressing a marker gene ("foci") on the bombarded filter. The number of cells in a focus which express the exogenous gene product 48 hours post-bombardment often range from 1 to 10 and average 2 to 3.

After effecting delivery of exogenous DNA to recipient cells by any of the methods discussed above, a preferred step is to identify the transformed cells for further culturing and plant regeneration. This step can include assaying cultures directly for a screenable trait or by exposing the bombarded cultures to a selective agent or agents.

An example of a screenable marker trait is the red pigment produced under the control of the R-locus in maize. This pigment can be detected by culturing cells on a solid support containing nutrient media capable of supporting growth at this stage, incubating the cells at, e.g., 18° C. and greater than 180 $\mu E\ m^{-2}s^{-1}$, and selecting cells from pigmented colonies (visible aggregates of cells). These cells can be cultured further, either in suspension or on solid media.

An exemplary embodiment of methods for identifying transformed cells involves exposing the bombarded cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing.

To use the bar-bialaphos selective system, bombarded cells on filters are resuspended in nonselective liquid medium, cultured (e.g. for one to two weeks) and transferred to filters overlaying solid medium containing from 1-3 mg/l bialaphos. While ranges of 1-3 mg/l will typically be preferred, it is proposed that ranges of 0.1-50 mg/l will find utility in the practice of the invention. The type of filter for use in bombardment is not believed to be particularly crucial, and can comprise any solid, porous, inert support.

Cells that survive the exposure to the selective agent can be cultured in media that supports regeneration of plants. Tissue is maintained on a basic media with hormones for about 2-4 weeks, then transferred to media with no hormones. After 2-4 weeks, shoot development will signal the time to transfer to another media.

Regeneration typically requires a progression of media whose composition has been modified to provide the appropriate nutrients and hormonal signals during sequential developmental stages from the transformed callus to the more mature plant. Developing plantlets are transferred to soil, and hardened, e.g., in an environmentally controlled chamber at about 85% relative humidity, 600 ppm $CO_2$, and 250 $\mu E\ m^{-2}s^{-1}$ of light. Plants are preferably matured either in a growth chamber or greenhouse. Regeneration will typically take about 3-12 weeks. During regeneration, cells are grown on solid media in tissue culture vessels. An illustrative embodiment of such a vessel is a petri dish. Regenerating plants are preferably grown at about 19° C. to 28° C. After the regenerating plants have reached the stage of shoot and root development, they can be transferred to a greenhouse for further growth and testing.

Genomic DNA can be isolated from callus cell lines and plants to determine the presence of the exogenous gene through the use of techniques well known to those skilled in the art such as PCR and/or Southern blotting.

Several techniques exist for inserting the genetic information, the two main principles being direct introduction of the genetic information and introduction of the genetic information by use of a vector system. A review of the general techniques can be found in articles by Potrykus ((1991) Annu. Rev. Plant Physiol. Plant Mol. Biol. 42:205-225) and Christou (Agri-Food-Industry Hi-Tech Mar./Apr. 17-27, 1994).

Thus, in one aspect, the present invention relates to a vector system that carries a construct encoding a zinc finger molecule or target DNA according to the present invention and that is capable of introducing the construct into the genome of a plant.

The vector system can comprise one vector, but it can comprise at least two vectors. In the case of two vectors, the vector system is normally referred to as a binary vector system. Binary vector systems are described in further detail in Gynheung An et al. (1980), Binary Vectors, Plant Molecular Biology Manual A3, 1-19.

One extensively employed system for transformation of plant cells with a given promoter or nucleotide sequence or construct is based on the use of a Ti plasmid from *A. tumefaciens* or a Ri plasmid from *Agrobacterium rhizogenes* (An et al. (1986) Plant Physiol. 81, 301-305 and Butcher et al. (1980) Tissue Culture Methods for Plant Pathologists, eds.:D. S. Ingrams and J. P. Helgeson, 203-208).

Several different Ti and Ri plasmids have been constructed that are suitable for the construction of the plant or plant cell constructs described above.

H. Examples of Specific Applications

Zinc fingers according to the invention can be used to regulate the expression of a nucleotide sequence of interest in the cell of a plant. Applications of the present invention include the overexpression or turning off of any desired target gene (which could be a gene or gene/s in a biosynthetic pathway or a transcription factor), or the investigation of the function of a gene in the plant. Some specific applications include the following:

1. Improvement of traits that are of interest to processors and end users of plants. For example, modifying the expression of genes involved in starch or oil biosynthesis (for example) will provide plants with improved processing and end-user characteristics.

2. Improvement in the plant use of inorganic nutrients. By modifying the expression of key enzymes involved in nutrient use, crop plants may be better able to grow in environments of lower nutrient availability or with the application of less inorganic fertilizer.

3. Improvement of other characteristics by manipulation of plant gene expression. Overexpression of the Na+/H+ antiport gene has resulted in enhanced salt tolerance in *Arabidopsis*. Targeted zinc fingers can be used to regulate the endogenous gene.

4. Improvement of ripening characteristics in fruit. A number of genes have been identified that are involved in the ripening process (such as in ethylene biosynthesis). Control of the ripening process via regulation of the expression of those genes will help reduce significant losses via spoilage.

5. Modification of plant growth characteristics through intervention in hormonal pathways. Many plant characteristics are controlled by hormones. Regulation of the genes involved in the production of and response to hormones will enable produce crops with altered characteristics.

6. Improvement of plant aroma and flavor. Pathways leading to the production of aroma and flavor compounds in vegetables and fruit are currently being elucidated allowing the enhancement of these traits using zinc finger technology.

7. Improving the pharmaceutical and nutraceutical potential of plants. Many pharmaceutically active compounds are known to exist in plants, but in many cases production is limited due to insufficient biosynthesis in plants. Zinc finger technology could be used to overcome this limitation by upregulating specific genes or biochemical pathways. Other uses include regulating the expression of genes involved in biosynthesis of commercially valuable compounds that are toxic to the development of the plant.

8. Reducing harmful plant components. Some plant components lead to adverse allergic reaction when ingested in food. Zinc finger technology could be used to overcome this problem by downregulating specific genes responsible for these reactions.

9. As well as modulating the expression of endogenous genes, heterologous genes can be introduced whose expression is regulated by zinc finger proteins. For example, a nucleotide sequence of interest can encode a gene product that is preferentially toxic to cells of the male or female organs of the plant such that the ability of the plant to reproduce can be regulated. Alternatively, or in addition, the regulatory sequences to which the nucleotide sequence is operably linked can be tissue-specific such that expression when induced only occurs in male or female organs of the plant. Suitable sequences and/or gene products are described in WO89/10396, WO92/04454 (the TA29 promoter from tobacco) and EP-A-344,029, EP-A-412,006 and EP-A-412,911.

The present invention will now be described by way of the following examples, which are illustrative only and non-limiting. The Examples show that a zinc finger chimera can be expressed in plants and recognize a determined sequence in a plant genome. Secondly, chimeras containing a trans-activating domain can activate the expression of a reported gene in plants in a manner similar to animal cells. Using this principle, zinc fingers can be designed to interact with specific sequences in plant genomes to either activate or repress the expression of genes of interest.

EXAMPLES

Materials and Methods
Gene Construction and Cloning.

In general, procedures and materials are in accordance with guidance given in Sambrook et al. Molecular Cloning. A Laboratory Manual, Cold Spring Harbor, 1989. The gene for the Zif268 fingers (residues 333-420) is assembled from 8 overlapping synthetic oligonucleotides (see Choo and Klug (1994)), giving SfiI and NotI overhangs. The genes for fingers of the phage library are synthesized from 4 oligo-nucleotides by directional end to end ligation using 3 short complementary linkers, and amplified by PCR from the single strand using forward and backward primers which contain sites for NotI and SfiI respectively. Backward PCR primers in addition introduce Met-Ala-Glu as the first three amino acids of the zinc finger peptides, and these are followed by the residues of the wild type or library fingers as required. Cloning overhangs are produced by digestion with SfiI and NotI where necessary. Fragments are ligated to 1 µg similarly prepared Fd-Tet-SN vector. This is a derivative of fd-tet-DOG1 (Hoogenboom et al. (1991) Nucl. Acids Res. 19:4133-4137) in which a section of the pelB leader and a restriction site for the enzyme SfiI (underlined) have been added by site-directed mutagenesis using the oligo-nucleotide:
5'CTCCTGCAGTTGGACCTGTGCCATGGC-CGGCTGGGCCGCATAGAATGG AACAAC-TAAAGC3' (SEQ ID NO: 3)
that anneals in the region of the polylinker. Electrocompetent DH5α cells are transformed with recombinant vector in 200 ng aliquots, grown for 1 hour in 2×TY medium with 1% glucose, and plated on TYE containing 15 µg/ml tetra-cycline and 1% glucose.

Figure 3:
FIG. 3, pBA002 and pER8.
Figure 3:
Figure 3:
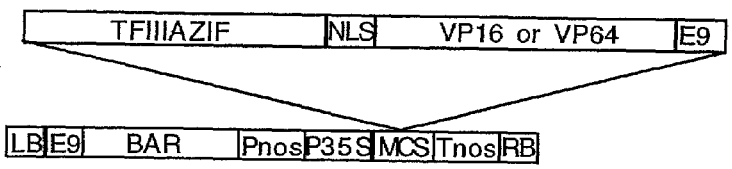
Figure 3:
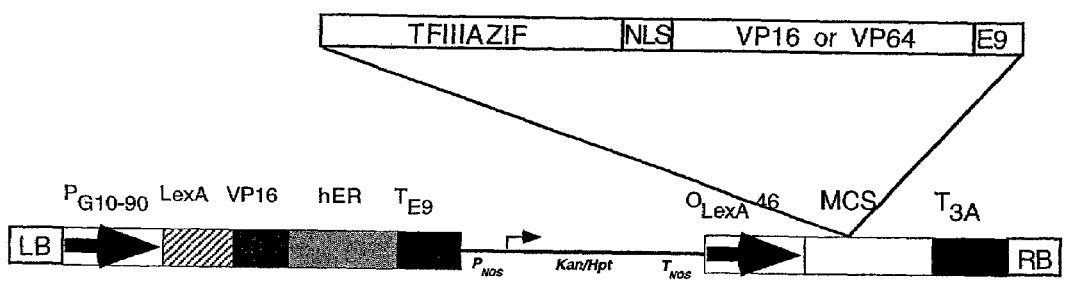

The zinc finger chimera that we used for this first set of experiments is a fusion protein that comprises 4 domain. First, 4 fingers of TFIIIA were linked through a spacer region to 3 fingers of Zif268 and this is denoted TFIIIAZif. Choo and Klug (1997) Curr. Opin. Str. Biol. 7:117-125; Pavletich and Pabo (1991) Science 252:809-817; Elrod-Erickson et al. (1996) Structure 4:1171-1180; and Elrod-Erickson et al (1998) Structure 6:451-464. This designed zinc finger is able to recognize specifically a DNA sequence of 27 base pair (bp). Second, a short region (NLS) that is a nuclear localization region rich in basic amino acids that directs the chimera to the nucleus. Third, a transactivation domain from the Herpes Simplex Virus (HSV) VP16 or VP64 that is a tetramer of the minimal VP16 domain. This region activates gene expression. Last, the 9E10 region that correspond to the myc domain for the specific antibody recognition of the expressed protein in plants (FIG. 3).

The reporter construct consists of a DNA monomer of the minimal binding site of 27 bp or tetramer of the minimal region that is recognized specifically by the zinc finger domain. This sequence is attached 5' to the 46 bp of the CaMV 35S minimal. Downstream of the promoter we have cloned the coding sequence luciferase or green fluorescent protein (GFP) genes as reporter genes. The luciferase from *Photinus pyralis* catalyzes the ATP/oxygen-dependent oxidization of substrate luciferin which produces the emission of light (bioluminescence) and the GFP fluoresces under blue light. At 3' end of the construct contains the pea rbcS-E9 polyadenylation sequence (FIG. 3).

The zinc finger phage display library of the present invention contains amino acid randomizations in putative base-contacting positions from the second and third zinc fingers of the three-finger DNA binding domain of Zif268, and contains members that bind DNA of the sequence XXXXXGGCG where X is any base. Further details of the library used can be found in WO98/53057.

Example 1

Generation of Transgenic Plants Expressing a Zinc Finger Protein Fused to a Transactivation Domain To investigate the utility of heterologous zinc finger proteins for the regulation of plant genes, a synthetic zinc finger protein was designed and introduced into transgenic *A. thaliana* under the control of a promoter capable of expression in a plant as described below. A second construct comprising the zinc finger protein binding sequence fused upstream of the Green Fluorescent Protein (GFP) reporter gene was also introduced into transgenic *A. thaliana* as described in Example 2. Crossing the two transgenic lines produced progeny plants carrying both constructs in which the GFP reporter gene was expressed demonstrating trans-activation of the gene by the zinc finger protein.

Using conventional cloning techniques, the following constructs were made as XbaI-BamHI fragments in the cloning vector pcDNA3.1 (Invitrogen). pTFIIIAZifVP16 pTFIIIAZifVP16 comprises a fusion of four finger domains of the zinc finger protein TFIIIA fused to the three fingers of the zinc finger protein Zif268. The TFIIIA-derived sequence is fused in frame to the translational initiation sequence ATG. The 7 amino acid Nuclear Localization Sequence (NLS) of the wild-type Simian Virus 40 Large T-Antigen is fused to the 3' end of the Zif268 sequence, and the VP16 transactivation sequence is fused downstream of the NLS. In addition, 30 bp sequence from the c-myc gene is introduced downstream of the VP16 domain as a "tag" to facilitate cellular localization studies of the transgene. While this is experimentally useful, the presence of this tag is not required for the activation (or repression) of gene expression via zinc finger proteins.

The sequence of pTFIIIAZifVP16 is shown in SEQ ID NO:4 as an XbaI-BamHI fragment. The translational initiating ATG is located at position 15 and is double underlined. Fingers 1 to 4 of TFIIIA extend from position 18 to position 416. Finger 4 (positions 308-416) does not bind DNA within the target sequence, but instead serves to separate the first three fingers of TFIIIA from Zif268 which is located at positions 417-689. The NLS is located at positions 701-722, the VP16 transactivation domain from positions 723-956, and the c-myc tag from positions 957-986. This is followed by the translational terminator TAA. pTFIIIAZifVP64 pTFIIIAZifVP64 is similar to pTFIIIAZifVP16 except that the VP64 transactivation sequence replaces the VP16 sequence of pTFIIIAZifVP16.

The sequence of pTFIIIAZifVP64 is shown in SEQ ID NO:5 as an XbaI-BamHI fragment. Locations within this sequence are as for pTFIIIAZifVP16 except that the VP64 domain is located at position 723-908 and the c-myc tag from positions 909-938.

The DNA binding site for the TFIIIAZif protein contains the DNA recognition sites for zinc fingers 1-3 of TFIIIA and the three zinc fingers of Zif 268. These are the DNA sequences GGATGGGAGAC (SEQ ID NO: 32) and GCGTGGGCGT (SEQ ID NO: 33), respectively. The six base pair sequence GTACCT in Sequence ID NO:3 is a spacer region of DNA that separates the two binding sites and the nucleotide composition of the DNA spacer appears to have no effect on binding of the protein. Therefore, this or other structured linkers could be used with other DNA spacers of different length and sequence.

The amino acid sequence of zinc Finger 4 of TFIIIA, including the flanking sequences as used in the composite protein of the invention, is
NIKICVYVCHFENCGKAFKKHNQLK VHQFSHTQQLP (SEQ ID NO: 28).

The nucleotide sequence of Zinc Finger 4 of TFIIIA, including the flanking sequences, is
AACATCAAGATCTGCGTCTATGTGTGCCATTTTGAG AACTGTGGCAAAGCATTCAAGAA ACACAATCAA 1TAAAGGTTCATCAGTTCAGTCACACACAGCAGC TGCCG (SEQ ID NO: 29).

Using conventional cloning techniques, the sequence 5'-AAGGAGATATAACA-3' (SEQ ID NO: 6) is introduced upstream of the translational initiating ATG of both pTFIIIAZifVP16 and pTFIIIAZifVP64. This sequence incorporates a plant translational initiation context sequence to facilitate translation in plant cells. Prasher et al. Gene 111:229-233 (1992); and Chalfie et al. Science 263:802-805 (1992).

The final constructs are transferred to the plant binary vector pBIN121 between the Cauliflower Mosaic Virus 35S promoter and the nopaline synthase terminator sequence. This transfer is effected using the XbaI site of pBIN121. The binary constructs thus derived are then introduced into *A. tumefaciens* (strain LBA 4044 or GV 3101) either by triparental mating or direct transformation.

Next, *A. thaliana* are transformed with *Agrobacterium* containing the binary vector construct using conventional transformation techniques. For example, using vacuum infiltration (e.g. Bechtold et al. CR Acad. Sci. Paris 316:1194-1199; Bent et al. (1994) Science 265:1856-1860), transformation can be undertaken essentially as follows. Seeds of *Arabidopsis* are planted on top of cheesecloth covered soil and allowed to grow at a final density of 1 per square inch under conditions of 16 hours light/8 hours dark. After 4-6 weeks, plants are ready to infiltrate. An overnight liquid culture of *Agrobacterium* carrying the appropriate construct is grown up at 28° C. and used to inoculate a fresh 500ml culture. This culture is grown to an $OD_{600}$ of at least 2.0, after which the cells are harvested by centrifugation and resuspended in 1 liter of infiltration medium (1 liter prepared to contain:2.2 g MS Salts, 1X B5 vitamins, 50 g sucrose, 0.5 g MES pH 5.7, 0.044 µM benzylaminopurine, 200 L Silwet µL-77 (OSI Specialty)). To vacuum infiltrate, pots are inverted into the infiltration medium and placed into a vacuum oven at room temperature. Infiltration is allowed to proceed for 5 mins at 400 mm Hg. After releasing the vacuum, the pot is removed and laid it on its side and covered with Saran™ wrap. The cover is removed the next day and the plant stood upright. Seeds harvested from infiltrated plants are surface sterilized and selected on appropriate medium. Vernalization is undertaken for two nights at around 4° C. Plates are then transferred to a plant growth chamber. After about 7 days, transformants are visible and are transferred to soil and grown to maturity.

Transgenic plants are grown to maturity. They appear phenotypically normal and are selfed to homozygosity using standard techniques involving crossing and germination of progeny on appropriate concentration of antibiotic.

Transgenic plant lines carrying the TFIIIAZifVP16 construct are designated At-TFIIIAZifVP16 and transgenic plant lines carrying the TFIIIAZifVP64 construct are designated At-TFIIIAZifVP64.

Example 2

Generation of Transgenic Plants Carrying a Green Fluorescent Protein Reporter Gene A reporter plasmid is constructed which incorporates the target DNA sequence of the TFIIIAZifVP16 and TFIIIAZifVP64 zinc finger proteins described above upstream of the Green Fluorescent Protein (GFP) reporter gene. The target DNA sequence of TFIIIAZifVP16 and TFIIIAZifVP64 is shown in SEQ ID NO:7.

This sequence is incorporated in single copy immediately upstream of the CaMV 35S -90 or -46 minimal promoter to which the GFP gene is fused.

The resultant plasmid, designated pTFIIIAZif-UAS/GFP, is transferred to the plant binary vector pBIN121 replacing the Cauliflower Mosaic Virus 35S promoter. This construct is then transferred to *A. tumefaciens* and subsequently transferred to *A. thaliana* as described above. Transgenic plants carrying the construct are designated At-TFIIIAZif-UAS/GFP.

Example 3

Use of Zinc Finger Proteins to Up-Regulate a Transgene in a Plant

To assess whether the zinc finger constructs TFIIIAZifVP16 and TFIIIAZifVP64 are able to transactivate gene expression in planta, *Arabidopsis* lines At-TFIIIAZifVP16 and At-TFIIIAZifVP64 are crossed to At-TFIIIAZif-UAS/GFP. The progeny of such crosses yield plants that carry the reporter construct TFIIIAZif-UAS/GFP together with either the zinc finger protein construct TFIIIAZifVP16 or the zinc finger construct TFIIIAZifVP64.

Plants are screened for GFP expression using an inverted fluorescence microscope (Leitz DM-IL) fitted with a filter set (Leitz-D excitation BP 355-425, dichronic 455, emission LP 460) suitable for the main 395 nm excitation and 509 nm emission peaks of GFP.

In each case, the zinc finger construct is able to transactivate gene expression demonstrating the utility of heterologous zinc finger proteins for the regulation of plant genes.

Example 4

Generation of Transgenic Plants Expressing a Zinc Finger Fused to a Plant Transactivation domain The constructs pTFIIIAZifVP16 and pTFIIIAZifVP64 utilize the VP16 and VP64 transactivation domains of Herpes Simplex Virus to activate gene expression. Alternative transactivation domains are various and include the C1 transactivation domain sequence (from maize; see Goff et al. (1991) Genes Dev. 5:298-309; Goff et al. (1992) Genes Dev. 6:864-875), and a number of other domains that have been reported from plants. Estruch et al. (1994) Nucl. Acids Res. 22:3983-3989.

Construct pTFIIAZifC1 is made as described above for pTFIIIAZifVP16 and pTFIIIAZifVP64 except the VP16/VP64 activation domains are replaced with the C1 transactivation domain sequence A transgenic *Arabidopsis* line, designated At-TFIIAZifC1, is produced as described above in Example 2 and crossed with At-TFIIIAZif-UAS/GFP. The progeny of such crosses yield plants that carry the reporter construct TFIIAZif-UAS/GFP together with either the zinc finger protein construct TFIIIAZifC1.

Plants are screened for GFP expression using an inverted fluorescence microscope (Leitz DM-IL) fitted with a filter set (Leitz-D excitation BP 355-425, dichronic 455, emission LP 460) suitable for the main 395 nm excitation and 509 nm emission peaks of GFP.

Example 5

Regulation of an Endogenous Plant Gene—UDP Glucose Flavanoid Glucosyl-Transferase (UFGT).

To determine whether a suitably configured zinc finger could be used to regulate gene transcription from an endogenous gene in a plant, the maize UDP glucose flavanoid glucosyl-transferase (UFGT) gene (the Bronze1 gene) was selected as the target gene. UFGT is involved in anthocyanin biosynthesis. A number of wild type alleles have been identified including Bz-W22 that conditions a purple phenotype in the maize seed and plant. The Bronze locus has been the subject of extensive genetic research because its phenotype is easy to score and its expression is tissue-specific and varied (for example aleurone, anthers, husks, cob and roots). The complete sequence of Bz-W22 including upstream regulatory sequences has been determined (Ralston et al. Genetics 119:185-197). A number of sequence motifs that bind transcriptional regulatory proteins have been identified within the Bronze promoter including sequences homologous to consensus binding sites for the myb- and myc-like proteins (Roth et al. Plant Cell 3:317-325). Identification of a zinc finger that binds to the bronze promoter The first step is to carry out a screen for zinc finger proteins that bind to a selected region of the Bronze promoter. A region is chosen just upstream of the AT rich block located at between -88 and -80, which has been shown to be critical for Bz1 expression (Roth et al. supra).

1. Bacterial colonies containing phage libraries that express a library of Zif268 zinc fingers randomized at one or more DNA binding residues are transferred from plates to culture medium. Bacterial cultures are grown overnight at 30° C. Culture supernatant containing phages is obtained by centrifugation.

2. 10 pmol of biotinylated target DNA, derived from the Bronze promoter, immobilized on 50 mg streptavidin beads (Dynal) is incubated with 1 ml of the bacterial culture supernatant diluted 1:1 with PBS containing 50 μM $ZnCl_2$, 4% Marvel, 2% Tween in a streptavidin coated tube for 1 hour at 20° C. on a rolling platform in the presence of 4 μg poly (d(I-C)) as competitor.

3. The tubes are washed 20 times with PBS containing 50 μM $ZnCl_2$ and 1% Tween, and 3 times with PBS containing 50 μM $ZnCl_2$ to remove non-binding phage.

4. The remaining phage are eluted using 0.1 ml 0.1 M triethylamine and the solution is neutralized with an equal volume of 1 M Tris-Cl (pH 7.4).

5. Logarithmic-phase *E. coli* TG1 cells are infected with eluted phage, and grown overnight, as described above, to prepare phage supernatants for subsequent rounds of selection.

6. Single colonies of transformants obtained after four rounds of selection (steps 1 to 5) as described, are grown overnight in culture. Single-stranded DNA is prepared from phage in the culture supernatant and sequenced using the Sequenase™ 2.0 kit (U.S. Biochemical Corp.). The amino acid sequences of the zinc finger clones are deduced.

Construction of a vector for expression of the zinc finger clone fused to a C1 activation domain in maize protoplasts Using conventional cloning techniques and in a similar manner to Example 1, the construct pZifBz23C1 is made in cloning vector pcDNA3.1 (Invitrogen).

pZifBz23C1 comprises the three fingers of the zinc finger protein clone ZifBz23 fused in frame to the translational initiation sequence ATG. The 7 amino acid Nuclear Localization Sequence (NLS) of the wild-type Simian Virus 40 Large T-Antigen is fused to the 3' end of the ZifBz23 sequence, and the C1 transactivation sequence is fused downstream of the NLS. In addition, 30 bp sequence from the c-myc gene is introduced downstream of the VP16 domain as a "tag" to facilitate cellular localization studies of the transgene.

The coding sequences of pZifBz23C1 are transferred to a plant expression vector suitable for use in maize protoplasts, the coding sequence being under the control of a constitutive CaMV 35S promoter. The resulting plasmid is termed pTMBz23. The vector also contains a hygromycin resistance gene for selection purposes.

A suspension culture of maize cells is prepared from calli derived from embryos obtained from inbred W22 maize stocks grown to flowering in a greenhouse and self pollinated using essentially the protocol described in EP-A-332104 (Examples 40 and 41). The suspension culture is then used to prepare protoplasts using essentially the protocol described in EP-A-332104 (Example 42).

Protoplasts are resuspended in 0.2 M mannitol, 0.1% w/v MES, 72 mM NaCl, 70 mM $CaCl_2$, 2.5 mM KCl, 2.5 mM glucose pH to 5.8 with KOH, at a density of about $2 \times 10^6$ per ml. 1 ml of the protoplast suspension is then aliquotted into plastic electroporation cuvettes and 10 μg of linearized pTMBz23 added. Electroporation is carried out s described in EP-A-332104 (Example 57). Protoplasts are cultured following transformation at a density of 2×10$^6$ per ml in KM-8p medium with no solidifying agent added.

Measurements of the levels UFGT expression are made using colorimetry and/or biochemical detection methods such as Northern blots or the enzyme activity assays described by Dooner and Nelson (1977) Proc. Natl. Acad. Sci. USA 74:5623-5627. Comparison is made with mock treated protoplasts transformed with a vector only control.

Alternatively, or in addition to, analyzing expression of UFGT in transformed protoplasts, intact maize plants can be recovered from transformed protoplasts and the extent of UFGT expression determined. Suitable protocols for growing up maize plants from transformed protoplasts are known in the art. Electroporated protoplasts are resuspended in Km-8p medium containing 1.2% w/v Seaplaque agarose and 1 mg/l 2,4-D. Once the gel has set, protoplasts in agarose are place in the dark at 26° C. After 14 days, colonies arise from the protoplasts. The agarose containing the colonies is transferred to the surface of a 9 cm diameter petri dish containing 30 ml of N6 medium (EP-A-332,104) containing 2,4-D solidified with 0.24% Gelrite®. 100 mg/l hygromycin B is also added to select for transformed cells. The callus is cultured further in the dark at 26° C. and callus pieces subcultured every two weeks onto fresh solid medium. Pieces of callus can be analyzed for the presence of the pTMBz23 construct and/or UFGT expression determined.

Corn plants are regenerated as described in Example 47 of EP-A-332,104. Plantlets appear in 4 to 8 weeks. When 2 cm tall, plantlets are transferred to ON6 medium (EP-A-332, 104) in GA7 containers and roots form in 2 to 4 weeks. After transfer to peat pots plants soon become established and can then be treated as normal corn plants.

Plantlets and plants can be assayed for UFGT expression as described above.

Example 6

Cloning of Zinc Finger Chimera in the Expression Vectors

In the following Examples, zinc finger chimeras specially designed for binding to specific DNA sequences in plants, were engineered with an effector domain (transactivator or repressor) and expressed in plants using a series of inducible gene expression system XVE or ZVE1. Aoyama and Chua (1997); and Zou and Chua (2000). Plant transformation was performed using standard procedures utilizing *Agrobacterium*.

Figure 2:
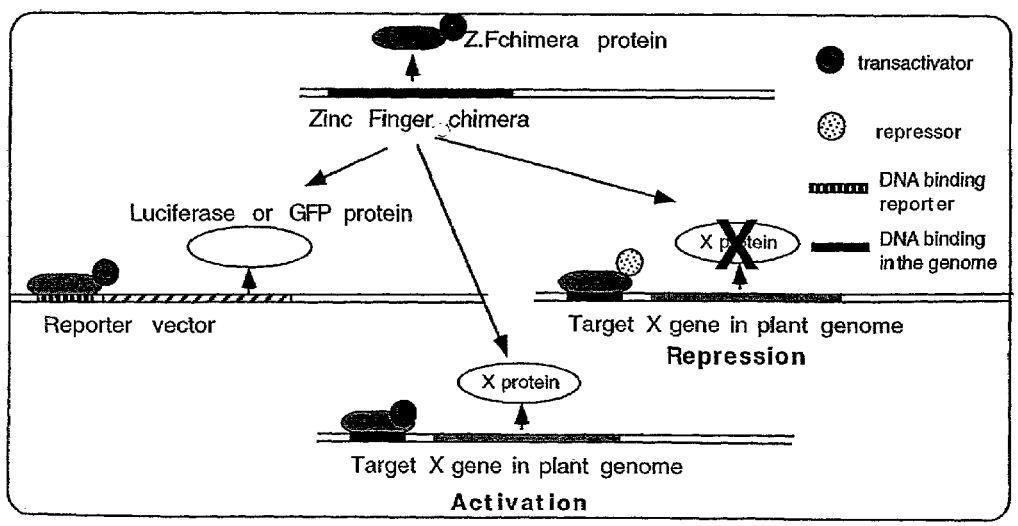
FIG. 2 is a more specific depiction of production of positive transgenic lines.

The general strategy is outlined in FIG. 1 and more specifically in FIG. 2.

The zinc finger chimeras were expressed either under the control of an estrogen receptor-based chemical-inducible system (binary vector pER8, Zuo et al. (2000) Plant J. 24:265-273) or the constitutive CaMV35S promoter (binary vector pBa002, Hajdukiewicz et al. (1994) Plant Mol. Biol. 25:989-994). The pBa002 plasmid was digested with MluI and SpeI (New England BioLabs, MA). The coding region of Zinc finger chimera genes (VP16 and VP64) were engineered by PCR to have a MluI restriction site at the 5' end and a SpeI site at the 3' end. The sequences of the forward and the reverse primers were 5'CCACGCGTCCATGGGAGAGAAGGCGCT-GCCGGTGG 3' (SEQ ID NO:8) and 5'CCACTAGTCCTTACAGATCTTCTTCA-GAAATAAGTTTTTGTTCC 3' (SEQ ID NO:9), respectively. The PCR-amplified DNA fragment was digested with MluI and SpeI, gel purified using the Qiaquick Gel extraction protocol (Qiagen, Valencia, Calif.), and ligated into the pBa002 plasmid using T4 DNA ligase (New England Biolabs, MA). A clone for each construct was verified by restriction analysis.

All constructs were introduced into *A. tumefaciens* strain ABI. Aoyama and Chua (1997). Similar procedures were used to clone the zinc finger chimeras (VP16 and VP64) into the AscI and SpeI sites. The coding region of each Zinc finger chimera gene (VP16 and VP64) was engineered by PCR to have an AscI restriction site at the 5' end and a SpeI site at the 3' end. Reporter construct pKL+1 plasmid was used for the construction of reporter plasmids. Foster and Chua (1999) Plant J. 17:363-372. pKL+1 plasmid contains a minimal promoter region from CaMV 35S promoter (−46 nucleotides) upstream of the luciferase coding sequence, that is terminated by pea rbcS-E9 polyadenylation sequence. The pKL+1 plasmid was digested with XbaI and HindIII (New England BioLabs, MA). A tetramer of the DNA binding site of the Zinc finger chimera was engineered by annealing two complementary oligos. The oligos were designed to have an XbaI restriction site at the 5' end and a HindIII site at the 3' end. The sequence of the sense and anti-sense strand primers were
5'CCTCTAGATCGGTCTCCCATCCAGGTA-
CACGCCCACGCAAGTCGGTCTC CCATCCAGGTA-
CACGCCCACGCAAGTCGGTCTCCCATC-
CAGGTACACGCCCACGCA
AGTCGGTCTCCCATCCAGGTACACGC-
CCACGCAAGAAGCTTCC3' (SEQ ID NO: 10)
and 5'GGAAGCTTCTTGCGTGGGCGTGTACCTG-
GATGGGAGACCGACTTGCGTG GGCGTGTAC-
CTGGATGGGAGACCGACT-
TGCGTGGGCGTGTACCTGGATGGGAGACC
GACTTGCGTGGGCGTGTACCTGGATGG-
GAGACCGATCTAGAGG3' (SEQ ID NO:11), respectively. The oligos were heated to 100° C. temperature for 5 min in TE (10 mM Tris-HCl pH8.5, EDTA 1 mM) solution containing 500 mM NaCl and cooled to room temperature. The annealed oligos were isolated from an agarose gel using the Qiaquick Gel extraction protocol (Qiagen, Valencia, Calif.). The double stranded DNA fragment was digested with XbaI and HindIII, gel purified using the Qiaquick Gel extraction protocol (Qiagen, Valencia, Calif.), and ligated into the pKL+1 plasmid using T4 DNA ligase (New England Biolabs, MA). A clone for each construct was verified by restriction analysis. Similar procedures were used to engineer a single binding site reporter construct except that the oligos used contained an XbaI restriction site at the 5' end and a HindIII site at the 3' end. The sequences of the forward and the reverse primers were 5'CCAGATCTGGTCTC-CCATCCAGGTACACGCCCACGCAAGATCTCC3' (SEQ ID NO:12) and
5'GGAGATCTTGCGTGGGCGTGTACCTG-
GATGGGAGACCAGATCTCGG3' (SEQ ID NO: 13), respectively.

For the versions of pKL+1 plasmid containing the GFP (green fluorescent protein) and RFP (red fluorescent protein), pKL+1 plasmid was digested with NcoI and KpnI for GFP and SalI and KpnI for RFP (New England Biolabs, MA). The coding region of GFP was engineered by PCR to have an NcoI restriction site at the 5' end and an EcoRI site at the 3' end. The sequences of the forward and the reverse primers were 5'CCCCATGGTGAGCAAGGGCGAGGAGCT-
GTTCACC3' (SEQ ID NO:14) and
5'CCGAATTCTTACTTGTACAGCTCGTC-
CATGCCGAG3' (SEQ ID NO:15), respectively. The coding region of RFP was engineered by PCR to have a SalI restriction site at the 5' end and an EcoRI site at the 3' end. The sequences of the forward and the reverse primers were
5'CCCTCGAGCGGGGTACCGCGGGCCCGGG3' (SEQ ID NO:16) and
5'CAGTTGGAATTCTAGAGTCGCGGCCGCTAC3' (SEQ ID NO:17), respectively.

Example 7

Construction of the pZVE Plasmids

The new binary transformation plasmid pER12 (Zuo et al. 2000) was modified by replacing the LexA DNA binding domain with the Zinc finger DNA binding domain (TFIIIAZif, FIG. 3). The coding region of the VP16-estrogen receptor was engineered by PCR to have XhoI restriction sites at both the 5' and 3' end. The sequences of the forward and the reverse primers were 5'CCGCTCGAGGC-CCCCCCGACCGATGTCAGCCTGGGGGA3' (SEQ ID NO:18) and 5'CCG CTCGAGTATTAATTTGAGAATGAA-CAAAAAGGACC3' (SEQ ID NO:19), respectively. The PCR-amplified DNA fragment was digested with XhoI, gel purified using the Qiaquick Gel extraction protocol (Qiagen, Valencia, Calif.), and ligated into the pTFIIIAZif plasmid (previously digested with XhoI) using T4 DNA ligase (New England Biolabs, MA). A clone was verified by restriction analysis and sequencing (pTFIIIAZif-VP16-ER). The coding region of the TFIIIAZif-VP16-estrogen receptor fusion gene was engineered by PCR to have an AseI restriction site at both the 5' and 3' end. The sequence of the forward and the reverse primers were 5'GCCATTAATCGGAATGG-GAGAGAAGGCGCTGCCGGTGG3' (SEQ ID NO:20) and 5'GCCTATTAATTTGAGAATGAACAAAAAGGACC3' (SEQ ID NO:21), respectively. pER12 plasmid was digested with AseI to removed the LexA-VP16-ER region. The PCR-amplified DNA fragment was digested with AseI, gel purified using the Qiaquick Gel extraction protocol (Qiagen, Valencia, Calif.), and ligated into the AseI-digested pER12 plasmid using T4 DNA ligase (New England Biolabs, MA). A clone was verified by restriction analysis and sequencing. The resulting plasmid (PER8 TFIIIAZif, see FIG. 3) containing Zinc finger fusion protein was digested with SalI to remove the hexamer of the LexA binding site.

Figure 4:
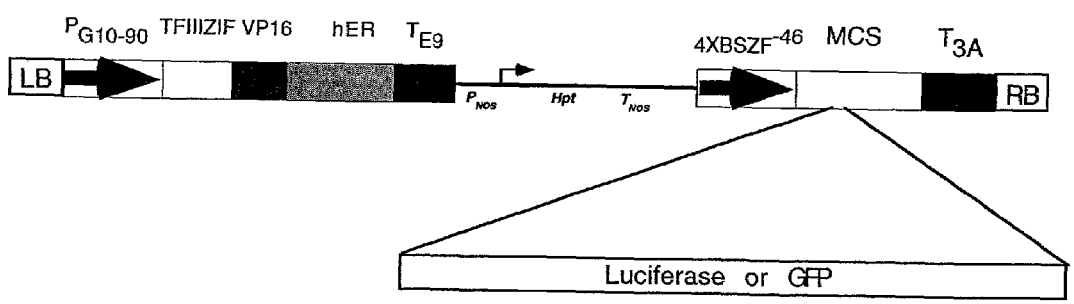
FIG. 4 depicts the component parts and final constructs of reporter constructs, and pZVE1.

The DNA fragment containing the plasmid was gel purified using the Qiaquick Gel extraction protocol (Qiagen, Valencia, Calif.), and ligated to a double strand tetramer of zinc finger DNA binding sites (previously digested with SalI) using T4 DNA ligase (New England Biolabs, MA). A clone was verified by restriction analysis and sequencing. The coding region of the GFP was engineered by PCR to have an XhoI restriction site at both the 5' and 3' end and cloned in the multiple cloning site of the vector (FIG. 4).

Example 8

Plant Transformation

*Arabidopsis thaliana* ecotype *Landsberg erecta* were transformed with *Agrobacterium* using the vacuum infiltration procedure according to Bent et al. (1994) Science 265:1856-1860. Seeds collected from the vacuum infiltrated plants were surface-sterilized by treatment with a solution of 1.5% sodium hypochlorite/0.01% Tween-20 (Sigma, St Louis Mo., USA) for 10 min and washing three times with sterile water. The sterilized seeds were then resuspended in 0.1% agarose and sown in Petri dishes containing A medium (full-strength Murashige and Skoog salts, pH 5.7, 1% sucrose, solidified with 0.8% Bactoagar, Gibco BRL, Grand Island, N.Y.) and 20 µg/ml hygromycin B (Sigma, St. Louis, Mo.). The plated seeds were vernalized for 4 d and then transferred to a growth chamber maintained at 22° C. under long day conditions (16 h light/8 hr dark). Transgenic T1 seedlings were selected on a plate containing hygromycin (20mg/ml) and after 2-3 weeks of growth the presence of the transgene was confirmed by PCR analysis. The results are presented in Table 1.

TABLE 1

| Constructs | Onion/Trans | Trans/Plants |
| --- | --- | --- |
| 35sVP16/4xBSLUC | Positive | — |
| 35sVP16/1xBSLUC | Positive | — |
| 35sVP64/4xBSLUC | Positive | — |
| 35sVP64/1xBSLUC | Positive | — |
| ERVP16/4xBSLUC | Positive(+) | T1 gene(few) |
| ERVP64/4xBSLUC | Positive(+) | T1 gene(few) |
| 4xBSLUC | — | T1 gene(good) |

Example 9

Estrogen Treatments

β17-Estradiol (Sigma, St Louis Mo.) was dissolved in dimethylsulfoxide (DMSO) to make a 100 mM stock solution. The solution was stored at −20° C. To monitor transgene expression, transgenic seeds were surface sterilized and sown in Petri dishes as described above. After vernalization at 4° C. for 4 days, the plates were incubated for two weeks in a growth chamber maintained at 22° C. under long day (16 hr light/8 hr dark) conditions. Seedlings were removed from the plates and grown for 2 days in a hydroponic system containing liquid A media (full-strength Murashige and Skoog salts, pH 5.7, 1% sucrose, Gibco BRL, NY, Dr. Takashi Aoyama personal communication). Fresh medium containing either β-17-Estradiol (30 µM) was added and plants were removed at the designated time points, and then washed and frozen in liquid nitrogen. For the vector control transgenic lines similar conditions were used and the experiments were performed in parallel.

RNA Analysis

Total RNA was isolated from seedlings and adult plants using the Qiagen RNA purification kit (Qiagen, Valencia, Calif.). RNA gel blot analysis was carried out according to the method described by Ausubel (1994). Each lane contained 10 µg of total RNA. The zinc finger gene, luciferase and 18S rDNA fragments were obtained by PCR amplification with Pfu polymerase as described above. Fragments were purified using the Qiaquick Gel extraction protocol (Qiagen, Valencia, Calif.). All DNA fragments were labeled with $^{32}$P-dCTP and $^{32}$P-dATP by random priming (Amersham, Arlington Heights, Ill.). Hybridization signals were quantified using the Phosphoimager STORM system (Molecular Dynamics) and the data analyzed with the Image Quant v1.1 program.

Light Microscope and Luciferase Imaging

The GFP and RFP fluorescent microscopy analysis was done using an Axioskop (Zeiss, Germany) according to methods described by Mayer et al. (1993). Onion peels and 3 week old seedlings were sprayed with 2.5 mM luciferin (Promega) containing 0.005% Triton X-100 and the luciferase activity monitored by photon counting. Video images (5 min) were captured in gravity mode using a intensifying CCD camera and coupling MethaMorph software (Universal Imaging Corporation PA). The results are presented in FIGS. 5-9.

Example 10

Results of Examples 6-9

Figure 5:
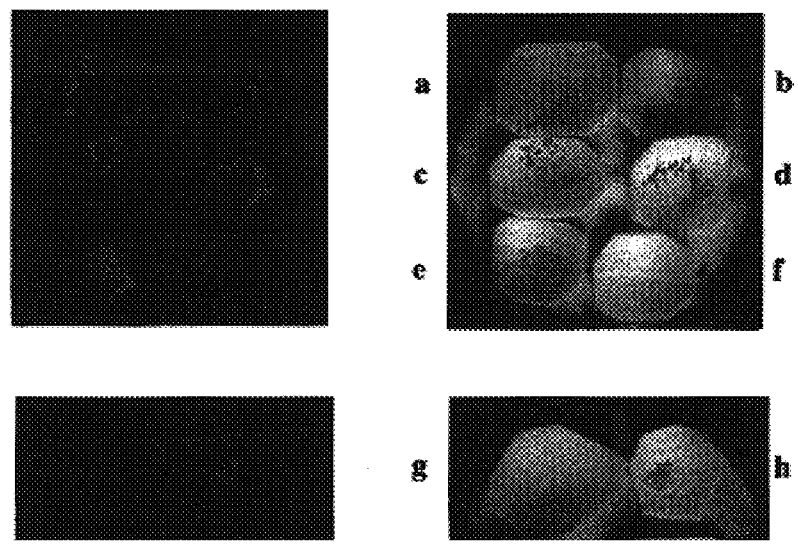
FIG. 5 shows transient expression of TFIIIAZIFVP16/VP64 and activation of luciferase reporter construct in onion peels by bombardment-mediated transformation.

In this series of experiments the zinc finger chimera, was cloned into the plant expression vector pBA002, placing its expression under the regulation of CaMVS35 promoter that it is constitutively expressed (see FIG. 3). The zinc finger chimera construct and the reporter construct were co-transformed into onion peels by biolistic bombardment with DNA-coated gold particles (BioRad, Oxford.UK). Transient expression of luciferase was recorded after 24 hr expression using an Imaging camera system. The results are shown in FIG. 5. The results reveal that expression of either zinc finger chimera containing VP16 or VP64 was able to induce strong expression of luciferase.

When tested with a reporter vector containing one binding site, the zinc finger chimera containing VP16 induced luciferase activity. In the absence of the zinc finger chimera the reporter vectors with either a single copy or tetramer of the minimal binding site alone produced only background levels of luciferase expression (FIG. 5).

In a second series of experiments, we used the XVE inducible system to express the zinc finger chimera and the reporter construct in onion peels and young *Arabidopsis* seedlings. The XVE system is an estrogen receptor-based chemical-inducible system for expression of genes in transgenic plants (FIG. 3).

Figure 6:
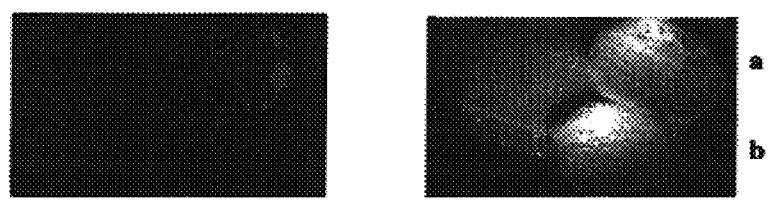
FIG. 6 shows 17-β-Estradiol (estrogen) regulated expression of luciferase.
Figure 6:
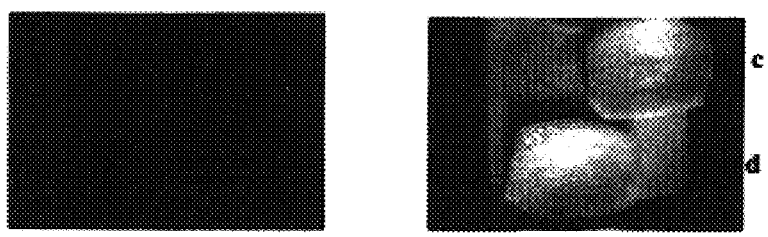

Briefly, a chimeric transcriptional activator XVE is a fusion protein of the DNA binding domain from the bacterial repressor LexA (X), the acidic transactivator domain VP16 (V) and the regulatory region of the human estrogen receptor (E, ER). The zinc finger chimera was cloned into the multiple cloning site (MCS) of the XVE vector downstream of eight copies of the LexA operator. The XVE was expressed by constitutive promoter G10-90 and in the presence of β-17-Estradiol the activated-XVE binds the LexA operator, inducing the expression of the zinc finger chimera. Similar experiments were done using the zinc finger chimera XVE construct, and the reporter constructs were transformed into two onion peels, only one of which was sprayed with β-17-Estradiol. The transient expression of luciferase was recorded after 24 hr expression, but only the onion peels sprayed with β-17-estradiol were able to display strong expression of luciferase (FIG. 6).

Figure 7:
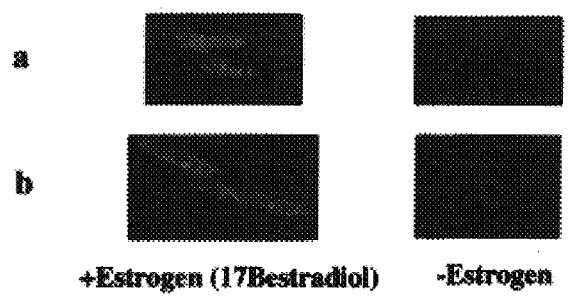
Figure 8:
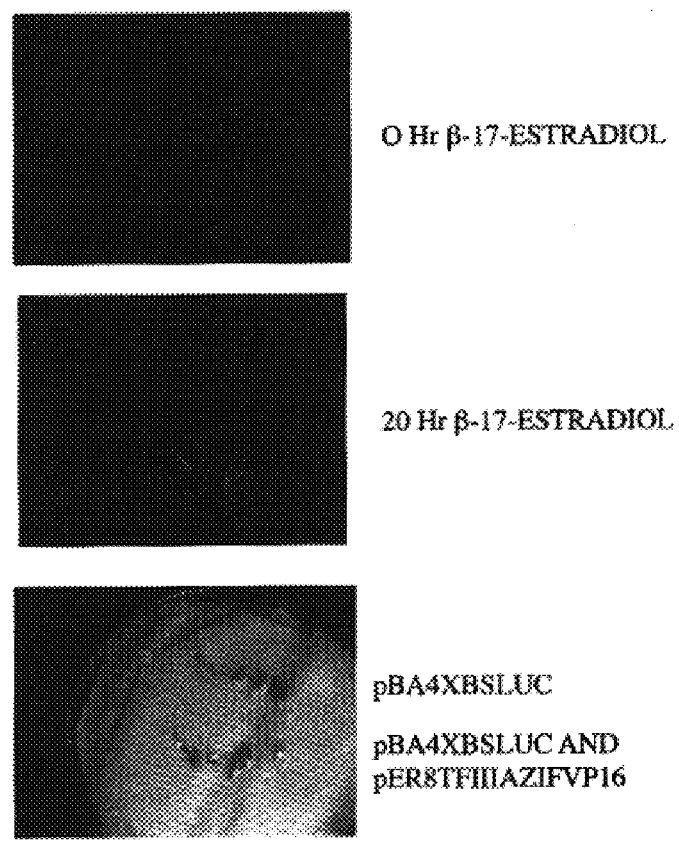
FIG. 8 depicts luciferase expression by induction of pER8-TFIIIAZIFVP16 in T1 transgenic plant leaves containing the pBA4XBSLUC and pER8-TFIIIAZIFVP16+p4XBSLUC.

Transformation of onion peels with the reporter vector alone containing tetramer of minimal binding site alone did not produce any luciferase expression with or without of β-17-estradiol. Similar results were obtained with a reporter construct containing GFP (FIG. 7). In addition, *Arabidopsis* plants were transformed with pBA4Xluciferase and pBA4Xluciferase+pER8TFIIIAZifVP16. Only transgenic (T1) lines leaves containing the zinc finger chimera XVE construct (pER8TFIIIAZifVP16) were able to produce luciferase expression with the addition of β-17-Estradiol (FIG. 8).

Figure 9:
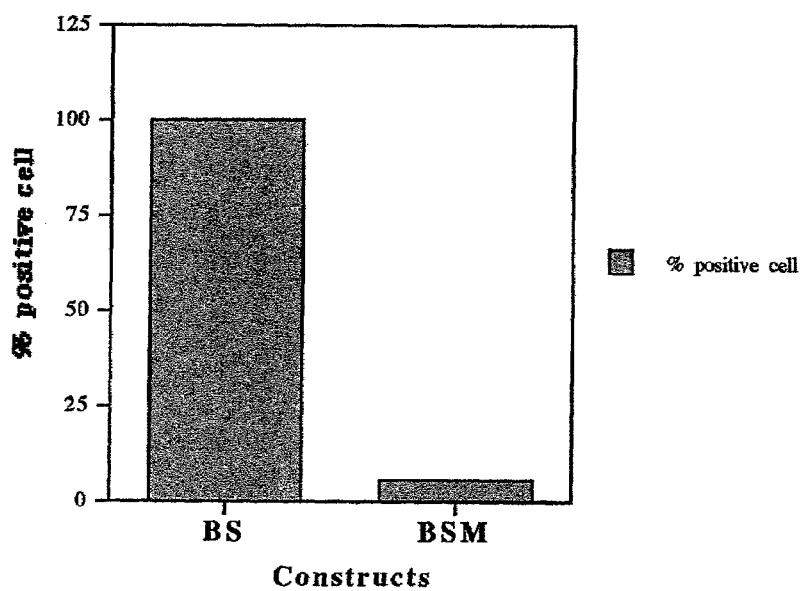
FIG. 9 depicts expression of 1XBSGFP and 1XBSMRFP in onion peels. The oligonucleotides are shown in SEQ ID NOS 30 & 31, respectively.

In a final experiment of the second series we tested the specificity of zinc finger chimera by offering two reporter constructs containing a 27 bp binding sequence upstream of GFP and the other with a single-mutated one 27 bp sequence binding sequence upstream of the RFP (Red fluorescence protein) cDNA. The single mutation in the 27 bp sequence binding sequence reduced the binding affinity of zinc finger chimera protein by 10-20 fold. Preliminary experiments done in onion peels showed a 201 fold difference in the percentage of transformed cells (FIG. 9). These constructs can be co-transformed with the inducible promoter zinc finger chimera into *Arabidopsis*.

Example 11

The XVE System

In another series, the Lex A binding domain of the XVE system (PER12) is replaced by the Zinc finger domain from the chimera (see FIG. 4) and the 8 LexA operator binding site by 4 minimal binding sites of the zinc finger. This new vector ZVE1 is tested by using either luciferase or GFP cloned in the same vector in transgenic *Arabidopsis* plants.

The invention claimed is:

1. A plant host cell or transgenic plant comprising
    (i) a polynucleotide encoding a zinc finger polypeptide comprising at least two zinc fingers, each zinc finger comprising a binding motif comprising the amino acid sequence shown in SEQ ID NO: 22; and
    (ii) a target DNA sequence in a plant gene, wherein at least one binding motif has been engineered to bind to the target DNA sequence.

2. The plant host cell or transgenic plant of claim 1 wherein the amino acid residue at position 1 of SEQ ID NO:22 is E, K, T, S, Q, V, A or P, the amino acid residue at position 23 of SEQ ID NO:22 is T or I, the amino acid residue at position 12 of SEQ ID NO:22 is S or T, there are two amino acids at positions 3-6 of SEQ ID NO:22, with the first of which being S, E, K, T, P, or R, and the second amino acid being E, and wherein the two zinc finger proteins are linked by the sequence shown in SEQ ID NO: 23 or SEQ ID NO: 24, and the amino acid residue at position 21 of SEQ ID NO:22 is Arg or Lys, and the amino acid residues at positions 14, 18 and 21 of SEQ ID NO:22 are hydrophobic amino acids and not Phe, Trp or Tyr.

3. The plant host cell or transgenic plant of claim 1 wherein one or more the zinc fingers binds to a target DNA triplet in accordance with the following:
    (a) if the 5' base in the triplet is G, then position 19 of SEQ ID NO:22 of the first zinc finger is Arg or position 15 of SEQ ID NO:22 of the second zinc finger is Asp or position 19 of SEQ ID NO:22 of the first zinc finger is Arg and position 19 of SEQ ID NO:22 of the first zinc finger is Asp;
    (b) if the 5' base in the triplet is A, then position 19 of SEQ ID NO:22 of the first zinc finger is Gin or Glu and position 15 of SEQ ID NO:22 of the second zinc finger is not Asp;
    (c) if the 5' base in the triplet is T, then position 19 of SEQ ID NO:22 of the first zinc finger in is Ser or Thr and position 15 of SEQ ID NO:22 of the second zinc finger is Asp or position 19 of SEQ ID NO:22 of the first zinc finger is a hydrophobic amino acid other than Ala;
    (d) if the 5' base in the triplet is C, then position 19 of SEQ ID NO:22 of the first zinc finger in may be any amino acid, provided that position 15 of SEQ ID NO:22 of the second zinc finger is not Asp;

(e) if the central base in the triplet is G, then position 16 of SEQ ID NO:22 is His;
(f) if the central base in the triplet is A, then position 16 of SEQ ID NO:22 is Asn;
(g) if the central base in the triplet is T, then position 16 of SEQ ID NO:22 is Ala, Ser, Ile, Leu, Thr or Val provided that if it is Ala, then one of the residues at position 13 or position 19 of SEQ ID NO:22 is a small residue;
(h) if the central base in the triplet is 5-meC, then position 16 of SEQ ID NO:22 is Ala, Ser, Ile, Leu, Thr or Val provided that if it is Ala, then one of the residues at position 13 or position 19 of SEQ ID NO:22 is a small residue;
(i) if the 3' base in the triplet is G, then position 13 is Arg;
(j) if the 3' base in the triplet is A, then position 13 is Gln and position 15 of SEQ ID NO:22 is Ala;
(k) if the 3' base in the triplet is T, then position 13 is Asn or position 13 is Gln and position 15 of SEQ ID NO:22 is Ser;
(l) if the 3' base in the triplet is C, then position 13 is Asp and position 14 of SEQ ID NO:22 is Arg; and,
when the central residue of a target triplet is C, the use of Asp at position 16 of SEQ ID NO:22 allows preferential binding to C over 5-meC.

4. The plant host cell or transgenic plant of claim 1 wherein there is an N-terminal zinc finger having a leader peptide as shown in SEQ ID NO: 27 added thereto.

5. The plant host cell or transgenic plant of claim 1 wherein one or more of the zinc fingers of the polypeptide comprises a mutated model zinc finger domain.

6. The plant host cell or transgenic plant of claim 5 wherein the model zinc finger domain is a zinc finger from a protein selected the group consisting of Zif268, GLI, Tramtrack, or YY1.

7. The plant host cell or transgenic plant of claim 5, wherein the zinc finger polypeptide has more than three zinc fingers.

8. The plant host cell or transgenic plant of claim 7 wherein the zinc finger polypeptide has four, five, six, seven, eight or nine zinc fingers.

9. The plant host cell or transgenic plant of claim 1, wherein the target DNA sequence is operably linked to a coding sequence.

10. The plant host cell or transgenic plant of claim 9, wherein transcription of the coding sequence is regulated by binding of the zinc finger polypeptide to the target DNA sequence.

11. The plant host cell or transgenic plant of claim 1, wherein the target DNA sequence is part of an endogenous sequence.

12. The plant host cell or transgenic plant of claim 9, wherein the target DNA sequence and the coding sequence are heterologous to the cell.

13. The plant host cell or transgenic plant of claim 1, wherein the zinc finger polypeptide is fused to a transcriptional activator domain.

14. The plant host cell or transgenic plant of claim 13 wherein the transcriptional activator domain comprises a VP16 transcriptional activator domain.

15. The plant host cell or transgenic plant of claim 13 wherein the transcriptional activator domain comprises a VP64 transcriptional activator domain.

16. The plant host cell or transgenic plant of claim 1, wherein the zinc finger polypeptide is fused to a transcriptional repressor domain.

17. The plant host cell of claim 1, wherein the zinc finger polypeptide is fused to a catalytic domain of a restriction enzyme.

18. The plant host cell or transgenic plant of claim 1 which is a transgenic plant.

19. The plant host cell or transgenic plant of claim 1 which is a plant host cell.

20. The plant host cell or transgenic plant of claim 1, wherein the second Cys residue is replaced by His.

* * * * *